(12) United States Patent
Lee

(10) Patent No.: US 7,494,644 B2
(45) Date of Patent: *Feb. 24, 2009

(54) METHODS AND COMPOSITIONS FOR CORRECTION OF CARDIAC CONDUCTION DISTURBANCES

(75) Inventor: Randall J. Lee, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 11/635,810

(22) Filed: Dec. 5, 2006

(65) Prior Publication Data

US 2008/0019953 A1   Jan. 24, 2008

Related U.S. Application Data

(63) Continuation of application No. 10/291,202, filed on Nov. 7, 2002, now Pat. No. 7,252,819.

(60) Provisional application No. 60/337,352, filed on Nov. 8, 2001.

(51) Int. Cl.
*A01K 48/00* (2006.01)

(52) U.S. Cl. ............... 424/93.21; 435/69.1; 435/320.1; 435/325

(58) Field of Classification Search ............ None
See application file for complete search history.

(56) References Cited

U.S. PATENT DOCUMENTS

| 5,030,204 | A | 7/1991 | Badger et al. |
|---|---|---|---|
| 5,087,243 | A | 2/1992 | Avitall |
| 5,103,821 | A | 4/1992 | King |
| 5,130,141 | A | 7/1992 | Law et al. |
| 5,489,294 | A | 2/1996 | McVenes et al. |
| 5,551,426 | A | 9/1996 | Hummel et al. |
| 5,661,133 | A | 8/1997 | Leiden et al. |
| 5,693,622 | A | 12/1997 | Wolff et al. |
| 5,709,854 | A | 1/1998 | Griffith-Cima et al. |
| 5,722,403 | A | 3/1998 | McGee et al. |
| 6,059,726 | A | 5/2000 | Lee et al. |
| 6,086,582 | A | 7/2000 | Altman et al. |
| 6,110,161 | A | 8/2000 | Mathiesen et al. |
| 6,113,571 | A | 9/2000 | Zinger et al. |
| 6,129,761 | A | 10/2000 | Hubbell |
| 6,151,525 | A | 11/2000 | Soykan et al. |
| 6,238,429 | B1 | 5/2001 | Markowitz et al. |
| 6,239,117 | B1 | 5/2001 | Christ et al. |
| 6,360,749 | B1 | 3/2002 | Jayaraman |
| 6,379,963 | B2 | 4/2002 | Haverich et al. |
| 6,387,369 | B1 | 5/2002 | Pittenger et al. |
| 6,415,178 | B1 | 7/2002 | Ben-Haim et al. |
| 6,932,804 | B2 | 8/2005 | Lee |
| 7,252,819 | B2* | 8/2007 | Lee ............ 424/93.21 |
| 2001/0009986 | A1 | 7/2001 | Ponzi |
| 2002/0001577 | A1 | 1/2002 | Haverich et al. |
| 2002/0013615 | A1 | 1/2002 | Haim et al. |
| 2002/0031501 | A1 | 3/2002 | Law |
| 2002/0044925 | A1 | 4/2002 | Law |
| 2002/0061295 | A1 | 5/2002 | Field |
| 2002/0061587 | A1 | 5/2002 | Anversa |
| 2002/0081728 | A1 | 6/2002 | Haverich et al. |
| 2003/0104568 | A1 | 6/2003 | Lee |
| 2004/0098075 | A1 | 5/2004 | Lee |
| 2006/0002898 | A1 | 1/2006 | Lee et al. |

FOREIGN PATENT DOCUMENTS

| EP | 1152053 | 11/2001 |
|---|---|---|
| WO | WO 90/10471 | 9/1990 |
| WO | WO 96/18303 | 6/1996 |
| WO | WO9702859 A1 | 1/1997 |
| WO | WO 98/02150 | 1/1998 |
| WO | WO 99/15211 | 4/1999 |
| WO | WO 01/68814 | 9/2001 |
| WO | WO0166472 | 9/2001 |
| WO | 02/19966 | 3/2002 |
| WO | WO 02/33111 | 4/2002 |
| WO | WO03039344 A2 | 5/2003 |
| WO | WO 03/094697 | 11/2003 |
| WO | WO 03/094855 | 11/2003 |
| WO | WO 03/095016 | 11/2003 |
| WO | WO 2004/045709 | 6/2004 |
| WO | WO 2004/050013 | 6/2004 |

OTHER PUBLICATIONS

American Heart Association. "2001 Heart and Stroke Statistical Update", Dallas, TX: American Heart Association, 1999.

Atkins, et al. "Cellular cardiomyoplasty improves diastolic properties of injured heart", *J. Surg. Res.*, (1999) vol. 85: 234-242.

Atkins, et. al. "Myogenic cell transplantation improves in vivo regional performance in infarcted rabbit myocardium" *Cardiac and Vascular* Regeneration, (2000) vol. 1: 43-53.

Atkins, et al. Cardiomyoplasty improves diastolic function in a rabbit model of myocardial injury, *Circulation*, (1998) vol. 98: Supplement 1: 1227.

(Continued)

*Primary Examiner*—Q. Janice Li
(74) *Attorney, Agent, or Firm*—Carol L. Francis; Gina C. Freschi; Bozicevic, Field & Francis LLP

(57) ABSTRACT

The invention provides methods for establishing electrical coupling between cardiomyocytes and recombinant cells which have been genetically engineered to express a connexin protein such as connexin 43 (Cx43) protein. The invention is based on the discovery that genetic modification of skeletal muscle cells to express a recombinant connexin, enables the genetically modified cells to establish electro-communication with cardiac cells via gap junctions. The recombinant connexin-expressing cells can be used for repair of cardiac tissue and for treatment of cardiac disease by transplantation into cardiac tissue.

11 Claims, 5 Drawing Sheets

OTHER PUBLICATIONS

Atkins, et. al. "Intracardiac transplantation of skeletal myoblasts yields two populations of striated cells in situ", *Ann Thorac Surg*, (1999) vol. 67: 124-129.

Atkins, et al. "Differential effects of cellular cardiomyoplasty on systolic and diastolic performance in cryoinjured rabbit heart", *J Heart Lung Transpl.*, (1999) vol. 18: 43.

Atkins, et al. "Transplanted autologous skeletal myoblasts improve myocardial performance after coronary artery ligation", *Cardiac and Vascular Regeneration*, (2000) vol. 1: 76-84.

Balogh, et al. "Expression of gap junction in cultured rat L6 cells during myogenesis", *Developmental Biology*, (1993) vol. 155: 351-360.

Blau. "Muscling in on gene therapy", *Nature*, (1993) vol. 364: 673-675.

Blau, et al. "Myoblasts in pattern formation and gene therapy", *Trends in Genetics*, (1993) vol. 9(8): 269-274.

Brittberg, et al. "Treatment of deep cartilage defects in the knee with autologous chondrocyte transplantation", *The New England J of Med.*, (1994) vol. 331: 889-895.

Chiu. "Cardiac cell transplantation: The autologous skeletal myoblast implantation for myocardial regeneration", *Adv Card Surg*, (1999) vol. 11: 69-98.

Chiu, et al. "Cellular cardiomyoplasty: Myocardial regeneration with satellite cell implantation", *Ann Thorac Surg*, (1995) vol. 60: 12-18.

Dahl, et al. "Expression of gap junction genes, connexin40 and connexin43, during fetal mouse development", *Anat. Embryol.*, (1995) vol. 191: 267-278.

Dai, et al. "Gene therapy via primary myoblasts: Long-term expression of factor IX protein following transplantation in vivo", *Proc. Natl. Acad. Sci. USA*, vol. 89: 10892-10895. 1992.

Dhawan, et al. "Systemic delivery of human growth hormone by injection of genetically engineered myoblasts", *Science*, (1991) vol. 254: 1509-1512.

Dorozynski. "Transplanted cells revive heart muscle", *British Medical Journal*, (2000) vol. 321(Issue 7268): 1040-1041.

El Oakley, et al. "Myocyte transplantation for myocardial repair: A few good cells can mend a broken heart", *Ann Thorac Surg.* (2001) vol. 71(5): 1724-1733.

Gage, et al. "Genetically modified cells: Applications for intracerebral grafting", *Trends in Neuroscience*, (1991) vol. 14(8): 328-333.

GenBank Accession No. AA511201 (Jul. 8, 1997).
GenBank Accession No. AA530689 (Jul. 22, 1997).
GenBank Accession No. AA822279 (Feb. 17, 1998).
GenBank Accession No. AA855990 (Mar. 6, 1998).
GenBank Accession No. AF151980 (Dec. 19, 2000).
GenBank Accession No. AH003191 (Sep. 6, 1995).
GenBank Accession No. M61896 (Mar. 11, 1994).
GenBank Accession No. M65188 (Nov. 1, 1994).
GenBank Accession No. N86403 (Apr. 1, 1996).
GenBank Accession No. NM_000165 (Accession first seen at NCBI on Mar. 24, 1999).
GenBank Accession No. NM_010288 (Accession first seen at NCBI on Jan. 26, 2000).
GenBank Accession No. NM_012567 (Accession first seen at NCBI on Feb. 15, 2000).
GenBank Accession No. X61576 (Nov. 8, 1991).
GenBank Accession No. X62836 (Nov. 7, 1996).

Gussoni, et al. "Normal dystrophin transcripts detected in Duchenne muscular dystrophy patients after myoblast transplantation", *Nature*, (1992) vol. 356: 435-438.

Husten. "Global epidemic of cardiovascular disease predicted", *Lancet*, (1998) vol. 352: 1530.

Janus, et al. "The modernization of Asia: Implications for coronary heart disease", *Circulation*, (1996) vol. 94: 2671-2673.

Kao, et al. "Satellite cell transplantation to repair injured myocardium", *Cardiac and Vascular Regeneration*, (2000) vol. 1: 31-42.

Kessler, et al. "Myoblast cell grafting into heart muscle: Cellular biology and potential applications", *Annu Rev Physiol*, (1999) vol. 61: 219-242.

Knudsen, et al. "A role for the $Ca^{2+}$-dependent adhesion molecule, N-cadherin, in myoblast interaction during myogenesis", *Exp. Cell Res.*, (1990) vol. 188: 175-184.

Koutouzis, et al. "Cell transplantation for central nervous system disorders", *Critical Reviews in Neurobio.*, (1994) vol. 8(3): 125-162.

Law, et al. "Cell transplantation as an experimental treatment for Duchenne muscular dystrophy", *Transplantation*, (1993) vol. 2: 485-505.

Lee, et al. "Coupling requirements for successful impulse propagation with skeletal myocytes transplanted in myocardium", *Annals of Biomedical Engineering*, (2000) vol. 28(Supp 1): S54: T6.10.

MacCalman, et al. "Noncoordinate developmental regulation of N-cadherin, N-CAM, integrin, and fibronectin mRNA levels during myoblast terminal differentiation", *Developmental Dynamics*, (1992) vol. 195: 127-132.

Marelli, et al. "Satellite cell implantation for neomyocardial regeneration", *Transplantation Proceedings*, (1992) vol. 24(6): 2995.

Menasché, et al. "Myoblast transplantation for heart failure", *Lancet*, (2001) vol. 357: 279-280.

Murray, et al. "Skeletal myoblast transplantation for repair of myocardial necrosis", *J Clin Invest*, (1996) vol. 98(11): 2512-2523.

Myerburg, et al. "Sudden cardiac death: Structure, function, and time-dependence of risk", *Circulation*. (1992) vol. 85(1): I2-I10.

Orlic, et al. "Bone marrow cells regenerate infracted myocardium", *Nature*, (2001) vol. 410: 701-705.

Peschanski, et al. "Bilateral motor improvement and alteration of L-dopa effect in two patients with Parkinson's disease following intrastriatal transplantation of foetal ventral mesencephalon", *Brain*, (1994) vol. 117: 487-499.

Pfeffer, et al. "Effect of captopril on progressive ventricular dilatation after anterior myocardial infarction", *New England J. of Med.*, (1988) vol. 319: 80-86.

Rajnoch, et al. "Cellular therapy reverses myocardial dysfunction", *J. Thoracic Cardiovascular Surgery*, (2001) vol. 121(5): 871-878.

Reinecke, et al. "Electromechanical coupling between skeletal and cardiac muscle: Implications for infarct repair", *J. Cell Biol.*, (2000) vol. 149(3): 731-740.

Reinecke, et al. "Transmural replacement of myocardium after skeletal myoblast grafting into the heart: Too much of a good thing?" *Cardiovasc Pathol.*, (2000) vol. 9(6): 337-344.

Robinson, et al. "Arterial delivery of genetically labeled skeletal myoblasts to the murine heart: Long-term survival and phenotypic modification of implanted myoblasts", *Cell Transplantation*, (1996) vol. 5(1): 77-91.

Scorsin, et al. "Comparison of the effects of fetal cardiomyocyte and skeletal myoblast transplantation on postinfarction left ventricular function", *J Thoracic Cardiovascular Surgery*, (2000) vol. 119: 1169-1175.

Soonpa, et al. "Formation of nascent intercalated disks between grafted fetal cardiomyocytes and host myocardium", *Science*, (1994) vol. 264: 98-101.

Springer, et al. "VEGF gene delivery to muscle: Potential role for vasculogenesis in adults", *Molecular Cell.*, (1998) vol. 2: 549-558.

Springer, et al. "High-efficiency retroviral infection of primary myoblasts", *Cell Mol. Genet.*, (1997) vol. 23 (3): 203-209.

Suzuki, et al. "Overexpression of connexin 43 in skeletal myoblasts: Relevance to cell transplantation to the heart", *J. Thoracic and Cardiovascular Surgery*, (2001) vol. 122(4): 759-766.

Tam, et al. "Molecular cardiomyoplasty: Potential cardiac gene therapy for chronic heart failure", *J. of Thoracic and Cardiovascular Surgery*, (1995): vol. 109(5): 918-924.

Taylor, et al. "Regenerating functional myocardium: Improved performance after skeletal myoblast transplantation", *Nature Medicine*, (1998) vol. 4(8): 929-933.

Taylor, et al. "Delivery of primary autologous skeletal myoblasts into rabbit heart by coronary infusion: A potential approach to myocardial repair", *Proceedings of the Association of American Physicians*, (1997) vol. 109:245-253.

Tremblay, et al. "Results of a triple blind clinical study of myoblast transplantations without immunosuppressive treatment in young boys with Duchenne muscular dystrophy", *Cell Transplantation*, (1993) vol. 2: 99-112.

Verheule, et al. "Characterization of gap junction channels in adult rabbit atrial and ventricular myocardium", *Cir. Res.*, (1997) vol. 80: 673-681.

Weisel, et al. "Cell transplantation comes of age", *J Thoracic Cardiovascular Surgery*, (2001) vol. 121(5): 835-836.

Zwiebel, et al. "Drug delivery by genetically engineered cell implants", *Annals of the New York Academy of Sciences*, (1991) vol. 618: 394-404.

Chachques, et al., "Cellular Therapy Reverses Myhocardial Dysfunction" 1st Virtual Congress of Cardiology. The American Association of Thoracic Surgery (Abst) 2000:202.

Field, et al., "Electrophysiological Modulation of Cardiomyocytic Tissue by Transfected Fibroblasts Expressing Potassium Channels" Circulation. 105:522-529 (2002).

Long, et al. "The Cardiac Fibroblast, Another Therapeutic target for Mending the Broken Heart" J. Mol Cell Cardiol. 34; 1273-1278 (2002).

Murry, et al., "Muscle Cell Grafting for the Treatment and Prevention of Heart Failure" J. of Cardiac Failure vol. 8 n0.6 Suppl (2002).

Long, Carlin S. et al, The Cardiac Fibroblast, Another Therapeutic Target For Mending The Broken Heart?; J of Molecular Cell Cardiology, vol. 34, pp. 1273-1278, Mar. 17, 2002.

Atkins, B. Zane et al, Myogenic Cell Transplantation Improves In Vivo Regional Performance . . . ; J Heart Lung Transplant 1999; 18:1173-1180. (Dec. 1999.

Reinecke H. et al. Gene Transfer of Connexin 43 into Skeletal Muscle, Human Gene Therapy, Jul. 2004, 627-636, vol. 15 (7).

Davis, et al., "Modulation of connexin43 expression: effects on cellular coupling", Journal of Cardiovascular Electrophysiology, 1995, vol. 6, No. 2, pp. 103-114.

Suzuki et al, "Overexpression of connexin 43 in skeletal myoblasts: relevance to cell transplantation to the heart", The Journal of Thoracic and Cardiovascular Surgery, 2001, vol. 122, No. 4, pp. 759-766.

Nicholas et al., "Immunocytochemical Analysis of Connexin Expression in the Healthy and Diseased Cardiovascular System", Microscopy Res. Technique. 2001, vol. 52, pp. 301-322.

Yang et al. VEGF Enhances Functional Improvement of Postinfarcted Hearts by Transplantation of ESC-Differentiated Cells. J. Appl. Physiol. 2002, vol. 93, pp. 1140-1151.

Khurana et al. Gene Therapy for Cardiovascular Disease. A Case for Cautious Optimis. Hypertension 2001, vol. 38, pp. 1210-1216.

Wang et al. Marrow stromal cells for cellular cardiomyoplasty: feasibility and potential clinical advantages. J Thorac Cardiovasc Surg, 2000, 120:999-1006.

Rook, et al. "Differences in gap junction channels between cardiac myocytes, fibroblasts, and heterologous pairs," American Physiological Society, 1992, p. C959-C977.

Fast et al. "Ansiotropic Activation Spread in Heart Cell Monolayers Assesed by High-Resolution Optical Mapping," Circulation Research, 1996, 79:115-127.

First ever transplantation of skeletal muscle cells to test whether the cells can repair damaged heart muscle. PR Newswire Sep. 25, 2000. www.prnewswire.com/cgi-bin/stories.pl?ACCT=104&STORY=/www/story/9-25-2000/0001321663&EDATE=.

* cited by examiner

METHODS AND COMPOSITIONS FOR CORRECTION OF CARDIAC CONDUCTION DISTURBANCES

CROSS-REFERENCE TO RELATED APPLICATION

This application claims the benefit of U.S. provisional application Ser. No. 60/337,352, filed Nov. 8, 2001 which application is incorporated herein by reference in its entirety.

STATEMENT REGARDING FEDERALLY SPONSORED RESEARCH

This invention was made with government support under grant nos. DK47766 awarded by the NIH. The government may have certain rights in this invention.

FIELD OF THE INVENTION

The invention relates generally to the field of treatment of cardiac conduction disturbances, more particularly to recombinant cell transplantation to facilitate cardiac tissue replacement or repair.

BACKGROUND OF THE INVENTION

Cardiac arrhythmias are a leading cause of morbidity in the Western hemisphere. The risk of developing malignant ventricular tachyarrhythmias is associated with the extent of myocardial injury and is believed to be the primary cause of approximately 50% of all cardiovascular deaths (Myerburg R J, Kessler K M, Castellanos A., Circulation January, (85) I suppl:I2-10, 1992.). Bradycardia and heart block, which can result from the normal aging process, further adds to the morbidity associated with cardiac arrhythmias and results in the permanent implantation of over 160,000 pacemakers annually in the United States.

Conventional medical therapy is predominantly palliative treatment and commonly fails to impede and prevent the morbidity and mortality associated with cardiac arrhythmias. Radiofrequency catheter ablation of ischemic ventricular tachycardias is considered adjuvant therapy rather than curative. The implantation of defibrillators and pacemakers, while generally effective, does have problems which include: (1) implantation of a mechanical device and its need for replacement every 4 to 7 years, (2) surgical and mechanical complications resulting from the implantation of the device, (3) negative physical and psychological effects of an implanted mechanical device and (4) a prevalent need to use concurrent antiarrhythmic therapy and/or radiofrequency modulation/ablation.

In some instances, and especially where the conduction disturbances are due to ischemia, only more radical options are available, such as surgery. However, even surgical techniques can fall well short of the therapeutic goal of restoring cardiac function in the patient. For example, coronary bypass surgery is frequently inadequate to restore function in patients who have few viable surviving myocytes in the infarct region. Therefore, there is a need to develop alternative therapies for treatment of myocardial dysfunction that overcome the negative aspects of current treatment methods. In contrast to the conventional treatment modalities which attempt to simulate the physiological process of the heart, the application of tissue engineering to correct conduction disturbances would enhance the natural physiological processes.

Tissue engineering techniques are attractive alternatives to such conventional therapies. Tissue engineering techniques generally involve transplanting cells that can imitate certain cardiac functions into cardiac tissue to effect myocardial repair (Soonpaa, M., Koh G Y, Klug M G, Field L J, Science, 1994. 264: p. 98-101; Orlic D, Kajstura J, Chimenti, S, Jakonluk I, Anderson S M, Li, B, Pickel J, McKay, R, Nadal-Ginard, B, Bodine, D, Leri A, Anversa P, Nature (2001) 410: 701-705. Chiu R C-J, Zibaitis A, Kao R L, Ann Thorac Surg (1995) 60:12-18).

Tissue engineering techniques involving, for example, transplantation of skeletal myoblasts to effect myocardial repair have gained increased attention with the demonstration that skeletal myoblasts survive and form contractile myofibers in normal and injured myocardium (Weisel R D et. al., J. Thoracic Cardiovascular Surgery 2001, 121:835-836; Murry, C., Wiseman R W, Schwartz S M, Hauschka S D, J Clin Invest, 1996. 98: p. 1512-2523; Murry C E, Wiseman R W, Schwartz S M, Hauschka S., J Clin Invest (1996) 98:2512-2523). Cell transplantation and tissue engineering of skeletal myoblast, and stem cells offer the promise of restoring function to patients with limited available myocytes. However, the emphasis of myocardial repair to date has focused on the preservation of myocardial contractility with little attention given to the effects of tissue engineering on cardiac conduction. One concern with the use of skeletal myoblasts transplantation for myocardial repair is whether the skeletal myoblasts will propagate electrical activity to cardiomyocytes.

Cardiomyocytes are electromechanically coupled by intercalated disks composed of adherens and gap junctions. N-cadherin is the major adherens junction protein, whereas connexin 43 (Cx43) is the major gap junction protein in the ventricular myocardium (Verheule S et. al., Circ. Res. 1997, 80:673-81). Due to the difference of cellular electrophysiological properties of cardiac cells and skeletal muscle cells, tight coupling of cardiac and skeletal muscle cells are required for synchronized electrical communication (Lee et al., Annals of Biomedical Engineering 28-1:S54, 2000).

Skeletal myoblasts express N-cadherin and connexin 43 as replicating myoblasts and then downregulate the expression of these two proteins after differentiation and myotube formation. Functional gap junctions have been detected during the early stages of skeletal muscle development, and gap junction intracellular communication has been suggested to play an important role in myoblast fusion and differentiation (MacCalman, C. D. et. al., Dev. Dyn. 1992, 195:127-132). Although multiple studies have shown that skeletal myoblasts survive cardiac grafting and form myotubes, these studies have not shown whether skeletal fibers form functional junctions with the surrounding cardiomyocytes allowing for electrical communication between the host and grafted cells. Most of these studies have indicated that connexin 43 (Cx43) and N-cadherin are not detectable in the skeletal muscle cells grafted into the host myocardium after cellular differentiation (myotube formation) by the lack of electromechanical coupling between grafted cells and myocardial cells (Murry C E et. al., J. Clin, Invest. 1996, 98:2512-2217; Robinson et. al., Cell Transplantation 1996, 5(1) 77-91; MacCalman, C. D. et. al., Dev. Dyn. 1992 195:127-132; Knudsen, K A et. al., Exp. Cell Res. 1990, 188:175-184; Balogh, S. et. al., Dev. Biol. 1993, 155:351-360; Dahl, E. et. al., Anat. Embryol. 1995, 191:267-278). Previous attempts to transplant skeletal muscle cells into myocardium have lacked the electrical coupling to cardiac cells which is necessary for myocardial coordinated activity.

When skeletal myoblasts and cardiomyocytes, or myotubes and cardiomyocytes, are co-cultured in vitro, the cells were found to be electromechanically coupled (Reinecke, H. et. al, J. Cell Biology, 2000, 149(3), 731-740). Reinecke et al. reported that cardiomyocytes were capable of forming electromechanical junctions with some skeletal myotubes in vitro and induced their synchronous contraction via gap junctions. N-cadherin and connexin 43 were both detected at the contact sites between cardiomyocytes and skeletal myotubes in this in vitro study, although the roles or importance of these proteins, or the mechanism involved, in forming gap junctions remained un-determined. While these studies exemplify the association of connexin 43 expression and functional gap junctions with cardiomyocytes in vitro, no evidence is presented which indicates that adult skeletal myocytes, which have minimal Cx43 expression, would be capable of forming functional gap junctions in cardiac tissue.

Accordingly, there is a need in the field to provide methods and compositions for induction and enhancement of the electrical coupling between cardiomyocytes and transplanted cells, such as adult skeletal muscle cells, to effect cardiac repair.

SUMMARY OF THE INVENTION

The invention provides methods for establishing electrical coupling between cardiomyocytes and recombinant cells which have been genetically engineered to express a connexin protein such as connexin 43 (Cx43) protein. The invention is based on the discovery that genetic modification of skeletal muscle cells to express a recombinant connexin, enables the genetically modified cells to establish electrocommunication with cardiac cells via gap junctions. The recombinant connexin-expressing cells can be used for repair of cardiac tissue and for treatment of cardiac disease by transplantation into cardiac tissue.

In one aspect the invention features a method of establishing an electrical connection between a recombinant mammalian cell and a myocardial cell, the method comprising contacting a myocardial cell with a recombinant mammalian cell genetically modified to produce a connexin protein, wherein contacting of the cells is in a manner sufficient to provide for production of an electrical connection between the myocardial cell and the recombinant cell. In specific embodiments, the recombinant cell is a skeletal muscle cell, a stem cell, a fibroblast, or a cardiac cell. In an embodiment of interest, the recombinant cell is a skeletal muscle cell, particularly an adult skeletal muscle cell or a myoblast cell. In embodiments of particular interest, the connexin protein is a connexin 43 protein.

In further embodiments, contacting involves implanting the recombinant cell into myocardial tissue of a subject. In further specific embodiments, the electrical connection between the recombinant cell and the myocardial cell is established, the recombinant cell has similar conductive characteristics similar to the myocardial cell.

In another aspect, the invention features a method of establishing an electrical connection between a recombinant skeletal muscle cell and a myocardial cell, the method comprising contacting a myocardial cell with a recombinant skeletal muscle cell genetically modified to express a recombinant connexin protein, where contacting is in a manner sufficient to provide for production of an electrical connection between the myocardial cell and the recombinant skeletal muscle cell. In specific embodiments, the skeletal muscle cell is an adult skeletal muscle cell or a skeletal myoblast cell. In still further embodiments, the electrical connection between the recombinant cell and the myocardial cell is established, the recombinant cell has similar conductive characteristics as the myocardial cell.

In still another aspect, the invention features a method of establishing an electrical connection between a recombinant skeletal muscle cell and a myocardial cell, the method comprising contacting a myocardial cell with a recombinant skeletal myoblast cell genetically modified to express a recombinant connexin 43 protein, wherein contacting is in a manner sufficient to provide for production of an electrical connection between the myocardial cell and the recombinant skeletal myoblast cell and the recombinant skeletal myoblast cell has similar conductive characteristics as the myocardial cell.

In another aspect the invention features a method for treating a cardiac conduction disturbance in a host, the method comprising introducing into cardiac tissue of a host a therapeutically effective amount of a recombinant mammalian cell, which recombinant cell is genetically modified to express a connexin protein, where introducing is effective to establish an electrical connection between the recombinant cell and a myocardial cell of the host cardiac tissue. In specific embodiments, the recombinant cell is a skeletal muscle cell, a stem cell, a fibroblast, or a cardiac cell.

Skeletal muscle cells, particularly an adult skeletal muscle cell or a myoblast cell are of particular interest. In still further embodiments, the connexin protein is a connexin 43 protein. In another embodiment, the recombinant cell is autologous to the host being treated. In related embodiments, introducing is accomplished by implanting the recombinant cell into an infarct region of the cardiac tissue.

In another aspect, the invention features a method for treating a cardiac conduction disturbance in a mammalian host, the method comprising introducing into cardiac tissue of the host a therapeutically effective amount of a skeletal muscle cell genetically modified to express a recombinant connexin 43 protein, where introducing is effective to establish an electrical connection between the introduced recombinant skeletal muscle cell and a myocardial cell of the host cardiac tissue, thereby treating the cardiac conduction disturbance. In specific embodiments, the skeletal muscle cell is an adult skeletal muscle cell or a myoblast cell. In related embodiments, introducing is accomplished by implanting the recombinant cell into an infarct region of the cardiac tissue. In a specific embodiment, the recombinant skeletal muscle cell is autologus to the host.

One other aspect of the invention involves a method of establishing an electrical connection between a recombinant transplanted cell and a myocardial cell. The method generally involves contacting a cell which has been genetically modified to produce a connexin protein, with a myocardial cell, in a manner that provides for production of an electrical connection between the myocardial cell and the genetically modified cell. In one embodiment of particular interest, the connexin protein is connexin 43.

In certain embodiments, the method generally involves contacting a recombinant mammalian cell genetically modified to produce a connexin protein (such as connexin 43), with a myocardial cell, in a manner that provides for production of a recombinant connexin (e.g. express or overexpress) connection between the myocardial cell and the recombinant cell, such that an electrical connection between the recombinant cell and the myocardial cell is established. In embodiments of particular interest, the contacting step involves implanting the recombinant cell into myocardial tissue of a subject in vivo. In certain embodiments, the recombinant cell is a skeletal muscle cell or myoblast cell, and in particular an adult skeletal muscle cell. The recombinant connexin protein (e. g.

connexin 43) is by the recombinant cell in sufficient amounts to induce and/or maintain an electrical connection between the recombinant cell and the myocardial cell. In certain embodiments the recombinant cell has similar conductive characteristics as the myocardial cell after the electrical connection between the recombinant cell and the myocardial cell is established. In one embodiment of particular interest, the connexin protein is connexin 43.

In another aspect, the invention features a method for improving conduction in cardiac tissue (e.g. so as treat cardiac disease) comprising introducing into cardiac tissue of a host a mammalian cell genetically modified to express a connexin protein, the introducing being effective to establish an electrical connection between the introduced genetically modified cell and a myocardial cell of the cardiac tissue, wherein conduction in the cardiac tissue is decreased. In certain embodiments, the method involves introducing a skeletal muscle cell genetically modified to express a connexin 43 protein. In specific embodiments the skeletal muscle cell is an adult skeletal muscle cell or a myoblast cell. In embodiments of particular interest, the host is human. In many instances, the introduction of a recombinant cell comprises surgically implanting the cell into an infarct region of the cardiac tissue for myocardial repair. In certain embodiments, the genetically modified cell originates from a biopsy from the host and the biopsy cell is genetically modified in vitro to express a recombinant connexin. In other embodiments the genetically modified cell is from a cell line which has been genetically modified in vitro to express a recombinant connexin protein.

These and other aspects, advantages and features of the present invention will become apparent to those persons skilled in the art upon reading the details of the invention more fully set forth below. The invention will now be described in further detail.

BRIEF DESCRIPTIONS OF THE DRAWINGS

FIGS. 1A-1D are graphical representations of the action potential parameters during different periods of myoblasts differentiation to myotubes. FIG. 1A: resting membrane potential (RMP) over 14 days; FIG. 1B: action potential amplitude (APA) over 14 days; FIG. 1C: maximum upstroke velocity (Vmax) over 14 days; FIG. 1D: action potential duration at 50% ($APD_{50}$) repolarization over 14 days.

Figure 4:
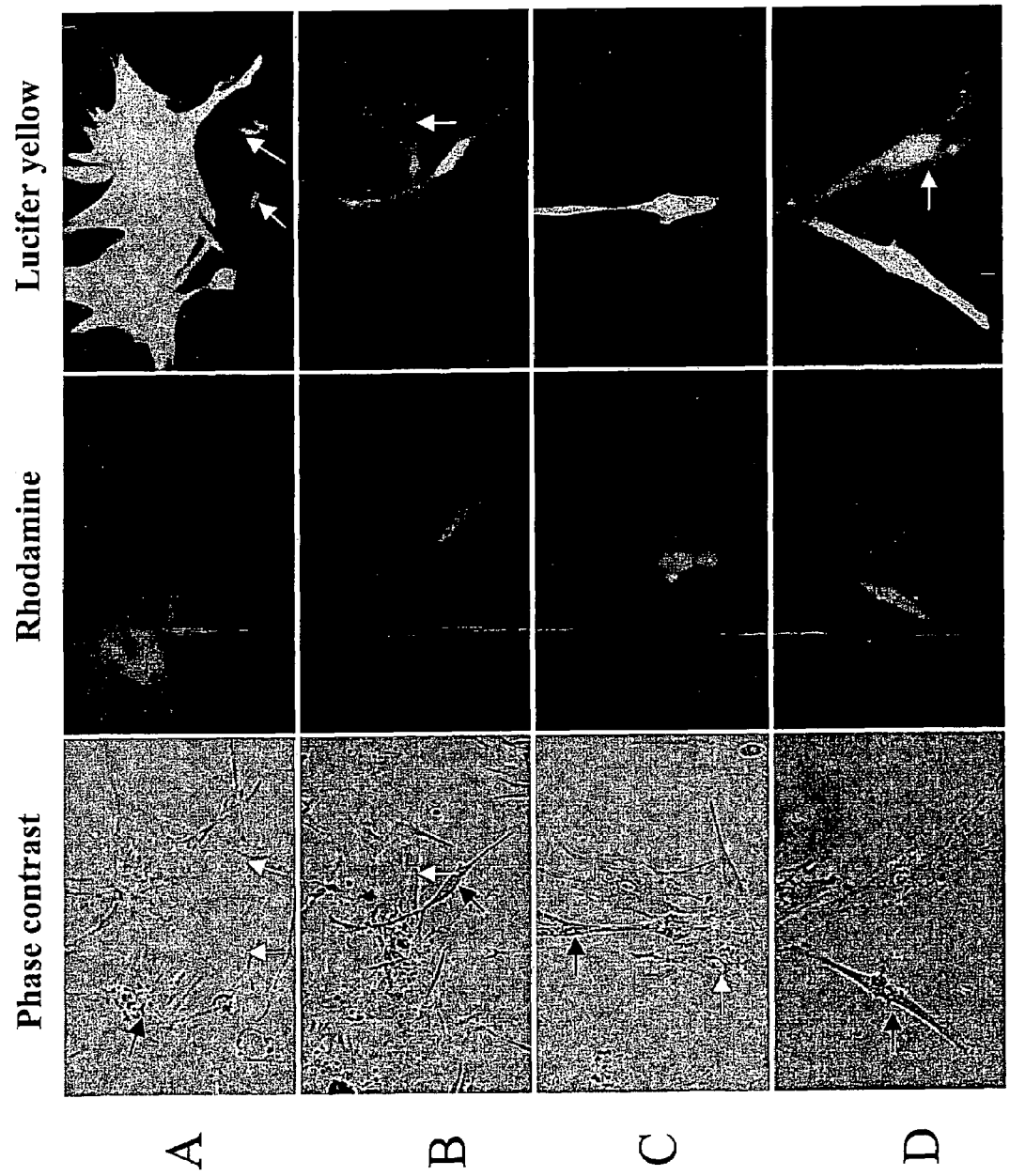

FIG. 4 is a series of photographs showing the results of a microinjection study between adult rat cardiomyoctyes (ARC) and skeletal myoblasts or myotubes. Injected cells were labeled with Rhodamine and Lucifer Yellow. Row A: ARC to control myoblasts; row B: ARC to recombinant Cx43-expressing cells; row C: ARC to control myotubes; row D: ARC to recombinant Cx43-expressing abnormal myotubes.

Figure 5:
Figure 5:
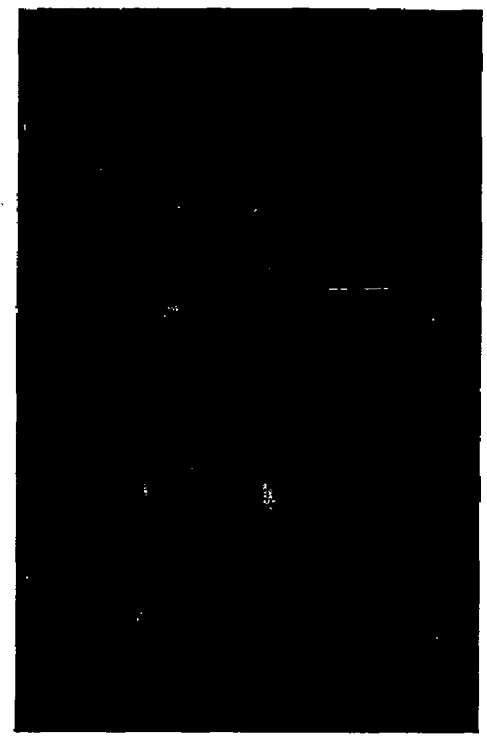
Figure 5:
Figure 5:

FIG. 5 is a series of photographs showing the results from an Immunofluorescence study analyzing the expression levels of MHC and Desmin, two strong markers for myoblast differentiation into myotubes, in control and Cx43 cells Before the present invention is described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural referents unless the context clearly dictates otherwise. Thus, for example, reference to "a cell" includes a plurality of such cells and functional equivalents thereof, and reference to "the polynucleotide" includes reference to one or more polynucleotides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated by reference for the purpose of describing and disclosing, for example, the cell lines, vectors, and methodologies which are described in the publications which might be used in connection with the presently described invention. The publications discussed herein are provided solely for their disclosure prior to the filing date of the present application. Nothing herein is to be construed as an admission that the inventors are not entitled to antedate such disclosure by virtue of prior invention.

DETAILED DESCRIPTION OF THE INVENTION

The present invention is based upon the discovery that contacting a myocardial cell with a recombinant cell, such as an adult skeletal muscle cell, which is modified to express a recombinant connexin 43 (e.g., in the presence or absence of endogenous connexin 43 expression) allows for electrical coupling of the modified skeletal muscle cell to the myocardial cell. The present invention thus provides methods for using a recombinant cell genetically modified to produce a connexin protein to produce persistent functional gap junctions between the recombinant cell and cardiomyocyte to obtain electrical communication between these cells. The use of recombinant cells that express recombinant Cx43 (or other connexin protein) increases and maintains the communication between the recombinant cells and myocardial cells, thus providing improved and coordinated electrical coupling with increased efficacy of myocardial contractility. The present invention provides methods of treatment of cardiac disease by transplanting or grafting recombinant cells modified to express a connexin into cardiac tissue to effect myocardial repair. Congestive heart failure is an exemplary cardiac disease that can be treated according to the methods of the invention.

Definitions

"Polynucleotide" as used herein refers to an oligonucleotide, nucleotide, and fragments or portions thereof, as well as to peptide nucleic acids (PNA), fragments, portions or antisense molecules thereof, and to DNA or RNA of genomic or synthetic origin which can be single- or double-stranded, and represent the sense or antisense strand. Where "polynucleotide" is used to refer to a specific polynucleotide sequence (e.g. a connexin 43 polypeptide-encoding polynucleotide), "polynucleotide" is meant to encompass polynucleotides that encode a polypeptide that is functionally equivalent to the recited polypeptide, e.g., polynucleotides that are degenerate variants (i.e., polynucleotides that encode the same amino acid sequence but differ in polynucleotide sequence due to the degeneracy of the genetic code), or polynucleotides that encode biologically active variants or fragments of the recited polypeptide, including polynucleotides having substantial sequence similarity or sequence identity relative to the sequences provided herein. Similarly, "polypeptide" as used herein refers to an oligopeptide, peptide, or protein. Where "polypeptide" is recited herein to refer to an amino acid sequence of a naturally-occurring protein molecule, "polypeptide" and like terms are not meant to limit the amino acid sequence to the complete, native amino acid sequence associated with the recited protein molecule, but instead is meant to also encompass biologically active variants or fragments, including polypeptides having substantial sequence similarity or sequence identify relative to the amino acid sequences provided herein.

As used herein, "polypeptide" refers to an amino acid sequence of a recombinant or non-recombinant polypeptide having an amino acid sequence of i) a native polypeptide, ii) a biologically active fragment of an polypeptide, iii) biologically active polypeptide analogs of an polypeptide, or iv) a biologically active variant of an polypeptide. Polypeptides useful in the invention can be obtained from any species, e.g., mammalian or non-mammalian (e.g., reptiles, amphibians, avian (e.g., chicken)), particularly mammalian, including human, rodenti (e.g., murine or rat), bovine, ovine, porcine, murine, or equine, preferably rat or human, from any source whether natural, synthetic, semi-synthetic or recombinant. For example, "Human connexin 43 polypeptide" refers to the amino acid sequences of isolated human Cx43 polypeptide obtained from a human, and is meant to include all naturally-occurring allelic variants, and is not meant to limit the amino acid sequence to the complete, native amino acid sequence associated with the recited protein molecule.

A "variant" of a polypeptide is defined as an amino acid sequence that is altered by one or more amino acids (e.g., by deletion, addition, insertion and/or substitution). Generally, "addition" refers to nucleotide or amino acid residues added to an end of the molecule, while "insertion" refers to nucleotide or amino acid residues between residues of a naturally-occurring molecule. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both. Guidance in determining which and how many amino acid residues may be substituted, added, inserted or deleted without abolishing biological or immunological activity can be found using computer programs well known in the art, for example, DNAStar software.

By "nucleic acid of interest" is meant any nucleic acid (e.g., DNA) which encodes a protein or other molecule which is desirable for inducing or maintaining electrical coupling between cells. In general, the nucleic acid is operatively linked to other sequences which are needed for its regulation and expression, such as a promoter and regulatory elements.

The term "biologically active" refers to, for example, a human connexin polypeptide having structural, regulatory, or biochemical functions of a naturally occurring connexin polypeptide, particularly with respect to facilitating the establishment of an electrochemical connection between a cell modified to express a connexin polypeptide and a myocardial cell. Likewise, "immunologically active" defines the capability of the natural, recombinant or synthetic human connexin polypeptide, or any oligopeptide thereof, to induce a specific immune response in appropriate animals or cells and to bind with a connexin specific antibody.

The term "derivative" as used herein refers to the chemical modification of a nucleic acid encoding a polypeptide or the encoded polypeptide. Illustrative of such modifications would be replacement of hydrogen by an alkyl, acyl, or amino group. A nucleic acid derivative would encode a polypeptide which retains essential biological characteristics of a natural polypeptide.

As used herein the term "isolated" is meant to describe a compound of interest (e.g., either a polynucleotide or a polypeptide) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound (e.g., either a polynucleotide or a polypeptide) that is removed from its natural environment and is at least 60% free, preferably 75% free, and most preferably 90% free from other components with which it is naturally associated.

By "transformation", "transduction" or "transfection" is meant a permanent or transient genetic change, preferably a permanent genetic change, induced in a cell following incorporation of new nucleic acid (e.g., DNA or RNA exogenous to the cell). Genetic change can be accomplished either by incorporation of the new nucleic acid into the genome of the host cell, or by transient or stable maintenance of the new DNA as an episomal element.

By "transformed cell", "transfected cell" or "transduced cell" is meant a cell into which (or into an ancestor of which) has been introduced, by means of recombinant DNA techniques, a DNA molecule encoding a protein of interest.

By "construct" is meant a recombinant nucleic acid, generally recombinant DNA, that has been generated for the purpose of the expression of a specific nucleotide sequence(s), or is to be used in the construction of other recombinant nucleotide sequences. Constructs useful in the invention are those which comprise connexin-encoding gene sequence operably linked to a promoter which will allow for the expression of the connexin protein in a transformed cell. Exemplary constructs useful for the expression of human and rat Cx43 in accordance with the invention are described in Shinoura, N, et al., J Neurosurg. 1996 May; 84(5):839-45 and Suzuki et al, Ann. Thorac. Surg., 2001, 71:1724-33, respectively.

By "promoter" is meant a minimal sequence sufficient to direct transcription in a recombinant cell. "Promoter" is also meant to encompass those elements sufficient for promoter-dependent gene expression controllable for cell-type specific, tissue-specific or inducible by external signals or agents; such elements may be located in the 5' or 3' regions of the native gene (e.g., enhancer elements).

By "operably linked" or "operatively linked" is meant that a DNA sequence and a regulatory sequence(s) are connected in such a way as to permit expression when the appropriate molecules (e.g., transcriptional activator proteins) are bound to the regulatory sequence(s).

By "connexin gene" is meant the open reading frame encoding a connexin polypeptide, or introns, or biologically active fragment thereof. "Connexin gene" includes adjacent 5' and 3' non-coding nucleotide sequences involved in the regulation of expression, up to about 10 kb beyond the coding region, but possibly further in either direction. The DNA sequences encoding a connexin may be cDNA or genomic DNA or a fragment thereof. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons (e.g., sequences encoding open reading frames of the encoded polypeptide) and 3' and 5' non-coding regions. Normally mRNA species have contiguous exons, with the intervening introns removed by nuclear RNA splicing, to create a continuous open reading frame encoding the polypeptide of interest.

By "cardiomyocyte" is meant a cardiac contractile cell, which is a cardiac muscle cell. The cardiomyocyte cell may be isolated and cultured in vitro or be part of the myocardium of a host.

By "skeletal muscle cell" is meant a cell found in skeletal muscle which includes but not limited to myoblasts, myotubes and mature skeletal muscle cells.

By "recombinant cell" is meant a cell comprising nucleic acid not normally associated with the cell (e. g. a cell transformed, transduced or transfected with a construct encoding a specific protein, e.g., a connexin protein).

By "transplanted cell" is meant a cell which has been introduced into a host so as to be in contact with a cell within a host. For example, a recombinant cell or cells may be grafted and/or implanted into the cardiac tissue of a host.

By "therapeutically effective amount" in the context of treatment of cardiac conduction disturbances is meant an amount effective to decrease a symptom of cardiac conduction disturbance and/or to improve cardiac conductance (a measure of conduction).

By "overexpressing" or "overexpression" of a gene product (such as a Cx43 protein) is meant an increased level of protein expression over a normal level of protein expression for a particular cell or cell type at, for example, a particular developmental stage or stage of differentiation. In certain instances, overexpressing can be a cumulative effect of protein expression from endogenous and recombinant genes or essentially protein expression from a recombinant gene. Overexpression of a connexin (e.g., Cx43) is meant to refer to the expression of connexin protein within a particular cell which is above the connexin expression level normally associated with a normal or wild-type cell at a particular stage of differentiation. For cells which normally do not express significant or detectable amounts of the connexin (e.g. as with Cx43 in adult skeletal muscle cells or myotubes), overexpression of connexin protein would mean any detectable expression of connexin, and particularly a level of expression sufficient to promote establishment of an electrochemical connection between the recombinant cell in which connexin expression is elevated and a cardiomyocyte. In certain embodiments overexpression of connexin is meant an increase in expression by a factor of at least about 2 fold, in other embodiments at least about 5 fold and yet in still other embodiments at least about 10 fold.

The terms "subject", "patient", "host" and "individual" are used interchangeably herein to refer to any mammalian subject for whom diagnosis or therapy is desired, particularly humans. Other subjects may include cattle, dogs, cats, guinea pigs, rabbits, rats, mice, horses, and so on. Of particular interest are subjects having a myocardial associated disorder that is amenable to treatment (e.g., to mitigate symptoms associated with the disorder) by the transplantation of cells which express a recombinant connexin (e.g., Cx43) into the subject (e.g., by introduction of a recombinant connexin expressing cell into the subject in vivo, or by grafting cells expressing a connexin (e.g., adult skeletal myoblasts, stem cells (e.g., mesenchymal, hematopoietic), fibroblasts, cardiac cells, etc.) into the subject. In many embodiments the hosts will be humans.

By "electrical coupling" is meant the interaction between cells which allows for intracellular communication between cells so as to provide for electrical conduction between the cells. Electrical coupling in vivo provides the basis for, and is generally accompanied by, electromechanical coupling, in which electrical excitation of cells through gap junctions in the muscle leads to muscle contraction.

By "cardiac conduction disturbance" is meant a disturbance in the normal generation and transmission of the electrical activity that initiates myocardial contraction. Cardiac arrhythmias resulting from electrical conduction disturbances can lead to life threatening ventricular tachyarrhythmias, hemodynamically compromising bradycardias, and heart block.

By "condition related to a cardiac conduction disturbance" is meant a condition, symptom or disorder associated with cardiac conduction disturbance. Examples of conditions related to cardiac conduction disturbance are irregular heart beat, fatigue, shortness of breath, and lack of synchronized heart muscle contraction.

By "treatment", "treating", or "treat" is meant that at least an amelioraton of the symptoms associated with the condition afflicting the host is achieved, where amelioration is used in a broad sense to refer to at least a reduction in the magnitude of a parameter, e.g. symptom (such as irregular heart beat, fatigue, shortness of breath, syncope can be symptoms associated with conduction disturbances as heart block, ventricular tachycardias or associated with congestive heart failure (i.e. lack of synchronized contraction)) associated with the condition being treated. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

Methods of Establishing Electrical Connection Between a Connexin-Overexpressing Cell and a Myocardial Cell The present invention provides methods for establishing an electrical connection between a recombinant cell expressing a connexin, and a myocardial cell. The methods generally involve contacting a connexin recombinant cell (e.g, a skeletal muscle cell, stem cell (e.g, mesenchymal, hematopoetic), fibroblast, cardiac cell, etc.) with a myocardial cell in a manner that provides for production of an eletrical connection between the myocardial cell and the recombinant cell. The cell is recombinant, e.g., it is genetically modified to produce a biologically active connexin protein, e.g., connexin 43

(Cx43) protein. Production of connexin in the recombinant cell provides for an electrical connection, and thus an electromechanical connection, between the recombinant cell and the myocardial cell.

Connexin-Encoding Nucleic Acids

As summarized above, the methods of the invention utilize nucleic acid compositions, including genomic and cDNA nucleic acid compositions, that encode biologically active connexin 43 proteins, or biologically active fragments, homologs, or analogues thereof suitable for expression in a recombinant cell which cell can subsequently form a electrochemical connection with a cardiac cell.

By "connexin protein" is meant a protein from the family of homologous proteins found in connexins of gap junctions as homo- or heterohexameric arrays. Connexin proteins are the major gap junction protein involved in the electrical coupling of cells. Gap junctions regulate intercellular passage of molecules, including inorganic ions and second messengers, thus achieving electrical coupling of cells. Over 15 connexin subunit isoforms are known, varying in size between about 25 kDa and 60 kDa and generally having four putative transmembrane α-helical spanners. Different connexins are specific for various parts of the heart. Connexin family proteins found in the cardiovascular system includes Cx37, Cx40, Cx43, and Cx45 (van Veen, A A; van Rijen, H V; Opthof, T., Cardiovascular Research 2001 Aug. 1, 51(2):217-29.; Severs, N J; Rothery, S; Dupont, E; Coppen, S R; Yeh, H I; Ko, Y S; Matsushita, T; Kaba, R; Halliday, D., Microscopy Research and Technique 2001 Feb. 1, 52(3):301-22; Kwong, K F; Schuessler, R B; Green, K G; Laing, J G; Beyer, E C; Boineau, J P; Saffitz, J E.,Circulation Research 1998 Mar. 23, 82(5):604-12).

As used interchangeably herein, "Connexin 43" and "Cx43" refer to the amino acid sequences of an isolated Cx43 polypeptide, having structural, regulatory, or biochemical functions associated with gap junctions and electromechanical coupling, obtained from any species, particularly mammalian, including human, rodenti (e.g., murine or rat), bovine, ovine, porcine, murine, or equine, preferably human, and may be natural, synthetic, semi-synthetic or recombinant, and is meant to include all naturally-occurring allelic variants, and is not meant to limit the amino acid sequence to the complete, native amino acid sequence associated with the recited protein molecule. Cx43 encompasses biologically active Cx43 fragments. Examples of Cx43 include human Cx43 (Genbank Accession Nos. XP_027460, XP_027459, XP_004121, P17302, AAD37802, A35853, NP_000156, AF151980, M65188, and AAA52131), mouse Cx43 (Genbank Accession Nos. P23242, P18246, A39802, A36623, NP_034418, NM_012567, NM_010288, CAA44640) and rat Cx43 are found at Genbank Accession Nos. P08050, S00532, NP_036699, AAA75194 and 1404339A.

A connexin genomic sequence of interest comprises the nucleic acid present between the initiation codon and the stop codon, with a connexin 43 gene being of particular interest, including all of the introns that are normally present in a native chromosome. It may further include the 3' and 5' untranslated regions found in the mature mRNA. It may further include specific transcriptional and translational regulatory sequences, such as promoters, enhancers, etc., including about 10 kb, but possibly more, of flanking genomic DNA at either the 5' or 3' end of the transcribed region. The genomic DNA may be isolated as a large fragment of 100 kbp or more, or as a smaller fragment substantially free of flanking chromosomal sequence. In another embodiment, the connexin DNA is a cDNA, which lacks intronic sequences that may be found in the genomic DNA. The cDNA may be operably linked to a promoter that is normally associated with the connexin sequence (e.g., a promoter endogenous to the connexin gene) or that is heterologous to the connexin sequence (i.e., a promoter from a source other than the connexin sequence).

The sequence of this 5' region, and further 5' upstream sequences and 3' downstream sequences, may be utilized for promoter elements, including enhancer binding sites, that provide for expression in tissues where the connexin polypeptide is normally expressed. The connexin sequence used can be based on the nucleotide sequences of any species (e.g., mammalian or non-mammalian (e.g., reptiles, amphibians, avian (e.g., chicken)), particularly mammalian, including human, rodent (e.g., murine or rat), bovine, ovine, porcine, murine, or equine, preferably rat or human) and can be isolated or produced from any source whether natural, synthetic, semi-synthetic or recombinant. Where the recombinant cell is a human cell, or where the cardiac tissue into which the cell is to be implanted is human, the connexin is preferably a human connexin or derived from a human connexin.

The nucleic acid compositions used in the subject invention may encode all or a part, usually at least substantially all, of the connexin polypeptide as appropriate. Fragments may be obtained of the DNA sequence by chemically synthesizing oligonucleotides in accordance with conventional methods, by restriction enzyme digestion, by PCR amplification, etc. For the most part, DNA fragments will be of at least about 100 contiguous nucleotides, usually at least about 200 nt, more usually at least about 250 nt to about 500 nt.

The connexin genes are isolated and obtained in substantial purity, generally as other than an intact mammalian chromosome. Usually, the DNA will be obtained substantially free of other nucleic acid sequences that do not include a sequence encoding a Cx43 or fragment thereof, generally being at least about 50%, usually at least about 90% pure and are typically "recombinant", i.e. flanked by one or more nucleotides with which it is not normally associated on a naturally occurring chromosome.

The sequence of the connexin protein, including flanking promoter regions and coding regions, may be mutated in various ways known in the art to generate targeted changes in promoter strength, sequence of the encoded protein, etc. The DNA sequence or product of such a mutation will be substantially similar to one or more of the sequences provided herein, i.e. will differ by at least one nucleotide or amino acid, respectively, and may differ by at least two, or by at least about ten or more nucleotides or amino acids. In general, the sequence changes may be additions, substitutions, insertions or deletions. Deletions may further include larger changes, such as deletions of a domain or exon. Such modified connexins sequences can be used, for example, to generate constructs for introduction into cells for the purpose of promoting production of electrochemical connections.

It should be noted that preferably the connexin gene is selected according to the genus and species of the host (e.g., where a human is to receive Cx43-modifed cells, then the Cx43 gene sequence is a human Cx43).

The encoded connexin is biologically active, e.g., when produced in a skeletal muscle cell, a biologically active Cx43 polypeptide facilitates establishment of a connection between the skeletal muscle cell and a myocardial cell. Without being held to theory, the connexin protein (e.g., Cx43) is expressed at the cell surface and is inserted into the plasma membrane as part of gap junctions. To establish electrical coupling between cells, connexin must be functional gap junctions to form gap junctional intercellular communication (GJIC). The identification of an electrical connection between two cells (e.g. such as an adult skeletal muscle cell and a myocardial cell) can be readily determined by those skilled in the art. Gap junctions can be evaluated by microinjecting cells with a gap junction permeable dye, e.g., Lucifer yellow (Molecular Probes, Oreg.), which is transferred from one cell to another when functional gap junctions are present. A micro injection protocol for detecting functional gap junctions (i.e. functional expression of Cx43) is given in the Examples section.

The recombinant cells can optionally be genetically modified to express other proteins, such as N-cadherin protein. However, the cells are preferably are not so modified so as to avoid additional genetic manipulation of the cell to be transplanted. Furthermore, the recombinant cell need not be modified to express or overexpress N-cadherin, as the inventors here have shown that expression of an exogenous (e.g., introduced or recombinant) connexin (either in the presence or absence of expression of any endogenous connexin) is sufficient.

Constructs For Connexin Nucleic Acids

Constructs comprising connexin nucleic acids are well known in the art. For example, constructs containing the connexin 43 gene are described by El Oakley, et al, Ann. Thorac. Surg., 2001, 71:1724-33. Constructs comprising connexin-encoding nucleic acids are utilized to transform, transfect or transduce specific cells of interest to allow for the expression of an introduced connexin-encoding nucleic acid molecule in the modified cell.

Where the nucleic acid to be expressed is DNA, any construct having a promoter (e.g., a promoter that is functional in a eukaryotic cell) operably linked to a DNA of interest can be used in the invention. The constructs containing the DNA sequence (or the corresponding RNA sequence) which may be used in accordance with the invention may be any expression construct suitable for use in a mammalian cell, and containing the DNA or the RNA sequence of interest. Such constructs can include nucleic acid of a plasmid or viral construct (e.g. adeno associated virus, adenovirus, and the liked) and can be circular or linear. Preferably the construct is capable of replication in eukaryotic and/or prokaryotic hosts. Suitable constructs are known in the art and are commercially available. The constructs can be prepared using techniques well known in the art. Likewise, techniques for obtaining expression of exogenous DNA or RNA sequences in a genetically altered host cell are known in the art.

In one embodiment, the DNA construct contains a promoter to facilitate expression of the DNA of interest within a mammalian cell. The promoter may be a strong promoter that functions in mamalian cells, such as a promoter from cytomegalovirus (CMV), mouse mammary tumor virus (MMTV), Rous sarcoma virus (RSV), lenti-virus or adenovirus. More specifically, exemplary promoters include the promoter from the immediate early gene of human CMV (Boshart et al., Cell 41:521-530, 1985) and the promoter from the long terminal repeat (LTR) of RSV (Gorman et al., Proc. Natl. Acad. Sci. USA 79:6777-6781, 1982). Alternatively, the promoter used may be a strong general eukaryotic promoter such as the actin gene promoter. In one embodiment, the promoter used may be a tissue-specific promoter. For example, the promoter used in the construct may be a cardiac cell specific promoter, a myoblast specific promoter or an adult skeletal muscle cell specific promoter (Luo, et. al., Development 2001 February, 128(4):459-69; Lee, et. al., J. Thor. Card. Sur. 1999 July, 118(1):26-4, discussion 34-5). Primary cardiac myocytes from neonatal rats have been transfected with a reporter construct driven by the C promoter of rat acyl-coenzyme synthetase gene (Kanda, et al. Heart Vessels 2000, 15(4):191-6) as well as alpha- and beta-cardiac myosin heavy chain gene promoters (James, et. al., Circulation 2000 Apr. 11, 101(14): 1715-21).

The constructs of the invention may also include sequences in addition to promoters which enhance and regulate connexin expression in modified cells. For example the serum response factor (SRF) gene has been shown to regulate transcription of numerous muscle and growth factor-inducible genes. Because SRF is not muscle specific, it has been postulated to activate muscle genes by recruiting myogenic accessory factors. Myocardin is a member of a class of muscle transcription factors, provides a mechanism whereby SRF can convey myogenic activity to muscle genes. (Wang, et. al., Cell. 2001 Jun. 29; 105(7):851-62).

In another embodiment, the promoter is a regulated promoter (e.g., inducible promoter), such as a tetracycline-regulated promoter, expression from which can be regulated by exposure to an exogenous substance (e.g., tetracycline). Another example of regulated promoter system useful in the present invention is the lac operator-repressor gene regulatory system to regulate mammalian promoters (Cronin, et. al., Genes Dev. 2001 Jun. 15, 15(12):1506-17).

For eukaryotic expression, the construct should contain at a minimum a eukaryotic promoter operably linked to a DNA of interest, which is in turn operably linked to a polyadenylation signal sequence. The polyadenylation signal sequence may be selected from any of a variety of polyadenylation signal sequences known in the art. An exemplary polyadenylation signal sequence is the SV40 early polyadenylation signal sequence. The construct may also include one or more introns, where appropriate, which can increase levels of expression of the DNA of interest, particularly where the DNA of interest is a cDNA (e.g., contains no introns of the naturally-occurring sequence). Any of a variety of introns known in the art may be used (e.g., the human ∃-globin intron, which is inserted in the construct at a position 5' to the DNA of interest).

In an alternative embodiment, the nucleic acid delivered to the cell is an RNA encoding a connexin protein. In this embodiment, the RNA is adapted for expression (i.e., translation of the RNA) in a target cell. Methods for production of RNA (e.g., mRNA) encoding a protein of interest are well known in the art, and can be readily applied to the product of RNA encoding connexin useful in the present invention.

Production of Recombinant Connexin Cells

Cells to be modified to express a recombinant connexin include any cell capable of coupling with a cardiomyocyte via connexin-mediated gap junctions, including skeletal muscle cells, stem cells (e.g., mesenchymal, hematopoietic), fibroblasts, cardiac cells, and the like, following genetic modification to provide for expression of a recombinant connexin (e.g., Cx43) in the cell. In one embodiment of particular interest, the cells are skeletal muscle cells.

Cells may be obtained from the host (e.g., endogenous cells) or from appropriate cultured cell lines. Cells may be autologous, allogeneic, or xenogeneic (e.g., primate, pig, etc.) with respect to the host. In certain embodiments, the cells are collected from the subject or patient via biopsy (e.g., muscle biopsy). This latter embodiment allows for autologous transplantation of recombinant connexin-expressing cells into host myocardium.

Cells suitable for use to produce recombinant connexin-expressing cells include skeletal muscle cells, particularly adult skeletal muscle cells, stem cells (e.g., mesenchymal, hematopoietic), fibroblasts, cardiac cells, and the like. An expression construct that provides for production of connexin (e.g., Cx43) is then introduced into the cells which may be propagated and cultured in vitro before and/or after transformation to increase the number of recombinant connexin-expressing cells available for transplantation into myocardial tissue.

In one embodiment, the cell is a skeletal cell muscle cell or cell line, propagated and transformed with an appropriate vector for the expression of a connexin (e.g., Cx43). These recombinant connexin expressing cells are cultured in vitro and utilized for transplantation into myocardium. In another embodiment, the cells are cells of a fresh primary culture or a frozen culture.

Methods for introducing connexin constructs into a mammalian cell include standard protocols known to those skilled in the art.

The regulation of connexin expression can be accomplished using regulatory elements operably inserted into the construct comprising the connexin gene used to transduce the modified cells. Other methods of regulating connexin expression may include genomic regulatory elements endogenous to the recombinant cells or by the addition of compounds that modulate connexin expression (e.g., either at the time of or following implanting the recombinant cells.)

Connexin expression in the modified cells can be detected by such techniques as western blotting, utilizing antibodies specific for the recombinant connexin. Other methods for confirming the expression of a recombinant connexin in transformed cells may involve RT-PCR utilizing primers specific for connexin mRNA or immunofluorescence techniques on transformed cells in culture. The ability of a connexin polypeptide, to facilitate production of an electrical connection between a recombinant cell and a cardiomyocyte can be tested in an in vivo model.

Production of Functional Gap Junctions Between Recombinant Connexin Cells and Cardiomyocytes The recombinant connexin-expressing cells can be cultured to expand the number of cells in vitro. After a desired number of recombinant cells are obtained, the cells are introduced into myocardial tissue. Alternatively or in addition, recombinant connexin cells and myocardial cells are co-cultured in vitro and then transplanted.

Production of a connexin allows the modified cells to induce an electrical connection with myocardial cells via gap junctions. Due to the difference in the cellular and electrophysiological properties of myocardial cells and non-myocardial cells, tight coupling of myocardial and non-myocardial cells is required for synchronized electrical communication. The present invention demonstrates a unique and novel interaction between two different cell types which allows for the treatment and therapy of myocardial diseases and disorders.

Methods of Treating Cardiac Conditions

The instant invention provides methods for correction of cardiac conduction disturbances and methods for treating cardiac conditions related to a cardiac conduction disturbance. The present invention is an advancement over standard cellular transplantation by increasing cell to cell communication, thus allow for more synchronized contraction. The methods generally involve contacting a cardiac tissue of a host with a recombinant cell that expresses a connexin protein (e.g., Cx43), such that the connexin protein facilitates production of an electrical connection between the recombinant cell and the cardiomyocyte. The connection facilitates correction of a cardiac conduction disturbance by improving conduction in the heart. In embodiments of particular interest, the recombinant cell is a skeletal muscle cell.

The subject methods find use in the treatment of a variety of different conditions in which an increase coordinated conduction of cardiomyocytes is desired.

Exemplary diseases amenable to treatment by the methods of the invention include, but are not limited to, complete heart block, reentrant arrhythmias (e.g., ventricular tachycardia) congestive heart failure, and the like. Any cardiac disease or disorder that would benefit from improved synchronized contraction is amenable to treatment with the methods of the present invention.

Implantation of Recombinant Connexin Cells

The transplantation of recombinant connexin cells into the myocardium of a subject can use well known surgical techniques for grafting tissue and/or isolated cells into a heart. In general, there are two methods for introducing the recombinant cells into the subject's heart tissue:1) surgical, direct injection; or 2) percutaneous techniques as describe in U.S. Pat. No. 6,059,726 (Lee and Lesh, "Method for locating the AV junction of the heart and injecting active substances therein").

The recombinant connexin cells can be implanted into any area of the heart where conduction disturbances have occurred. The amount of recombinant cells to be transplanted is determined by the type of heart disease being treated, the overall damage of myocardial tissue and the level of connexin expression in the cells to be transplanted.

In certain embodiments, the recombinant connexin-expressing cells are transplanted by percutaneous methods. If the site of the damaged heart tissue can be accurately determined in a subject by non-invasive diagnostic techniques, the recombinant connexin cells can be injected directly into the damaged myocardial tissue using general methods for percutaneous injections into cardiac muscle well known in the art. The amount of recombinant cells necessary to be therapeutically effective will vary with the type of disorder being treated as well as the extent of heart damage that has occurred.

Immunosuppressants may be used in conjunction of transplantation of Cx43-overexpressing cells not derived from the host to minimize the possibility of graft rejection, e.g., allogeneic or xenogeneic cells.

Combination with Other Therapies

The methods of the subject invention may also be utilized in combination with other cardiac therapies when appropriate. In certain embodiments, drugs used to treat certain types of conduction defects can be administered in combination with implanting recombinant connexin cells into the damaged myocardium (e.g., prior to, during and/or after implantation). Cardiac drugs that are suitable for use in combination therapy with the methods of the invention include, but are not limited to, growth factors, polynucleotides encoding growth factors, angiogenic agents, calcium channel blockers, antihypertensive agents, antimitotic agents, inotropic agents, anti-atherogenic agents, anti-coagulants, beta-blockers, anti-arrhythmic agents, antiinflammatory agents, vasodilators, thrombolytic agents, cardiac glycosides, antibiotics, antiviral agents, antifungal agents, agents that inhibit protozoans, anti-arrhythmic agents (used for treatment of ventricular tachycardia), nitrates, angiotensin converting enzyme (ACE) inhibitors; brain natriuretic peptide (BNP); antineoplastic agents, steroids, and the like.

The present invention may also be a supplemental procedure to coronary artery bypass grafting (CABG). Replacement of a non-functioning myocardial scar with functioning muscle together with revascularization improves myocardial performance more than revascularization (bypass surgery) alone. Transplantation of recombinant connexin cells in conjunction with CABG provides for additive treatment during surgery by preventing the continued myocardial remodeling by reducing wall stress and ischemic burden. Additional surgical procedures to deliver the recombinant cells into the myocardium can be avoided by implanting the recombinant cells at the time of CABG surgery.

Assessment of Therapy

The effects of therapy according to the methods of the invention can be monitored in a variety of ways. Generally for heart block disorders, an electrocardiogram (ECG) or holter monitor is utilized to determine the efficacy of treatment. The contraction of the heart occurs due to electrical impulses that are generated within the heart; an ECG is a measure of the heart rhythms and electrical impulses. Thus ECG is a very effective and non-invasive way to determine if therapy has improved or maintained, prevented, or slowed degradation of the electrical conduction in a subject's heart. The use of a holter monitor, a portable ECG that can be worn for long periods of time to monitor heart abnormalities, arrhythmia disorders, and the like, is also a reliable method to assess the effectiveness of therapy.

Electrophysiology tests which involve percutaneous placement of catheters within the heart to assess the conduction properties of the heart, can also be used to assess therapy.

Where the condition to be treated is congestive heart failure, an echocardiogram or nuclear study can be used to determine improvement in ventricular function. Comparison of echocardiograms prior to and after the grafting of recombinant connexin cells into myocardial tissue allows for reliable assessment of treatment.

The above methods for assessing the efficacy of therapy are only exemplary and are not meant to be limiting. Many appropriate assays for detecting synchronized coupling, (e.g., by monitoring cardiac function) are well known in the art and can be adapted for use.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Example 1

Characterization of Skeletal Myoblasts/Myotubes Ability to Electrically Excite Cardiac Tissue Tissue engineering techniques are attractive alternatives to conventional therapies for the treatment of end stage heart disease and conduction abnormalities. Cell transplantation offers the promise of restoring function to patients.

Biopsied skeletal muscle have satellite cells, skeletal myoblasts, which are able to divide and multiply. Skeletal myoblasts initially express Cx43. However, as the cells mature and differentiate into myotubes (the basic unit which leads to the contractile muscle fiber), Cx43 expression is the least in the skeletal myotubes.

Skeletal myoblasts and myotubes have different cellular electrophysiological characteristics. Characterization of the action potential parameters during different periods of myoblasts differentiation to myotubes were determined. Skeletal myoblasts were isolated by enzymatic dispersion from the hind limb muscle of 2-5 day old neonatal rats. Myoblasts were differentiated into multinucleated myotubes in culture by replacing the growth medium with differential medium (DM). (98% DMEM, 2% horse serum (HyClone), penicillin G 100 U/ml and streptomycin 100 µg/ml). Myoblasts and myotubes incubated in DM 2-14 days were studied. Whole cell configuration of patch clamp technique was used to record action potentials. The following measurements were obtained: resting membrane potential (RMP), action potential amplitude (APA), action potential duration at 50% ($APD_{50}$) repolarization (Table 1).

Myoblasts began to differentiate into multinucleated myotubes in 4 days and form a network of spontaneously contractile fibers by 10-14 days.

TABLE 1

Change of action potential parameters during different days in DM

| group | RMP (mV) | APA (mV) | Vmax (V/s) | Threshold (nA) | $APD_{50}$ (ms) |
|---|---|---|---|---|---|
| DM 2 (n = 10) | −27.4 ± 2.9 | 60.1 ± 5.8 | 27.4 ± 4.2 | 31.1 ± 6.5 | 15.1 ± 1.7 |
| DM 4 (n = 4) | −38.3 ± 3.6 | 94.4 ± 6.5 | 72.2 ± 6.7 | 23.8 ± 2.39 | 8.1 ± 0.1 |
| DM 6 (n = 8) | −50.6 ± 3.0 | 113.9 ± 3.4 | 102.9 ± 9.0 | 18.1 ± 0.9 | 7.4 ± 0.5 |
| DM 8 (n = 11) | −52.8 ± 1.8 | 123.7 ± 4.3 | 123.5 ± 6.4 | 17.2 ± 1.9 | 7.4 ± 0.4 |
| DM 10 (n = 7) | −53.1 ± 2.5 | 133.1 ± 2.7 | 153.4 ± 8.9 | 29.2 ± 5.3 | 7.4 ± 0.5 |
| DM 11 (n = 10) | −53 ± 1.7 | 133.5 ± 3.1 | 146.4 ± 2.9 | 33 ± 2.8 | 5.1 ± 0.5 |
| DM 12 (n = 9) | −52.4 ± 3.2 | 127.4 ± 2.9 | 142.7 ± 6.4 | 30.7 ± 6.8 | 5.4 ± 0.7 |
| DM 13 (n = 9) | −48.8 ± 3.1 | 120.6 ± 3.0 | 129.3 ± 6.8 | 30 ± 4.9 | 7.5 ± 0.6 |
| DM 14 (n = 9) | −46.8 ± 0.9 | 120.2 ± 5.4 | 114.6 ± 3.9 | 43.3 ± 4.3 | 6.4 ± 0.6 |

Freshly isolated skeletal myoblasts did not have measurable action potentials and were unable to be electrically stimulated.

Figure 1A:
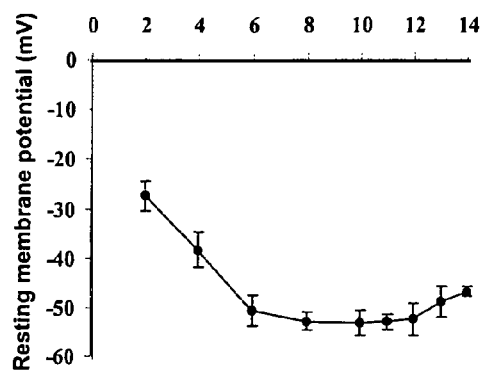

RMP. There was no significant difference between days 8 and days 10-14 (FIG. 1A).

Figure 1B:
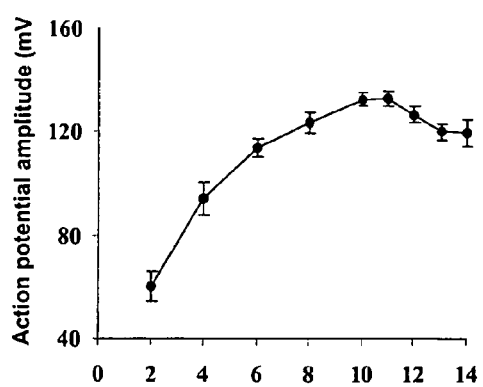

APA: With the RMP of myotube becoming more negative during development, the amplitude of action potential also increased and reached to a peak value at 10-11 days. Then, APA decreased in parallel until 13-14 days. No significant difference was found between day 10 and day 8, day 11-14. (FIG. 1B)

Figure 1C:
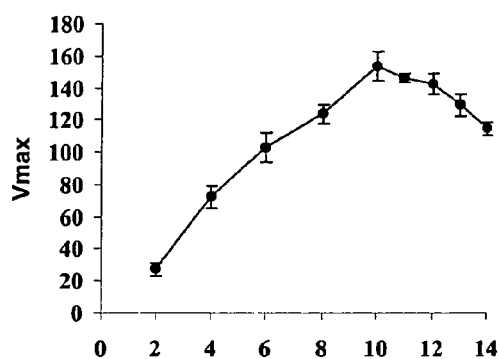

Vmax: similar changes were noticed as that of APA. (FIG. 1C)

Figure 1D:
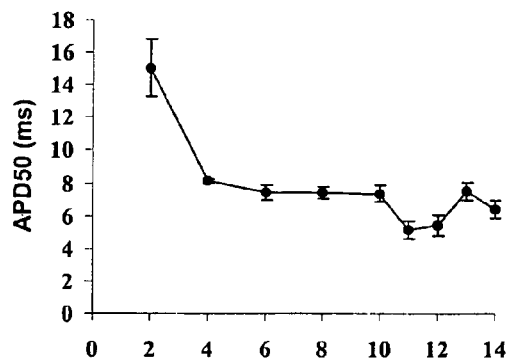

$APD_{50}$: The minimum value of $APD_{50}$ occurred at 11-12 days and then increased. There was no significant among each group except day 2. (FIG. 1D).

Thus, action potential parameters change during different periods of myoblasts differentiation to myotubes.

The patch clamping data highlights the relative electrical inexcitability of myoblasts in DM less than 7 days. The implications of these results is that transplanted skeletal myoblasts/myotubes will not propagate an electrical impulse unless there is enhanced cellular coupling via gap junctions.

Computer modeling was used to assess cell to cell electrical excitation between skeletal myoblasts and myofibers with cardiac myocardial cells (Lee R et al., Annals of Biomedical Engineering 28-1:S54, 2000). The modeling was performed by incorporating measured cellular parameters of each cell's type. The computer modeling results determined that the action potential duration (APD) of skeletal cells is short (1.6 ms and 2.8 ms for myoblast and myofiber, respectively), as compared to the cardiac cell, and is the major limitation of skeletal-to-skeletal and skeletal-to-cardiac excitation. A high degree of intercellular coupling was required for skeletal cells to excite their downstream neighbors quickly enough, within 2.5 ms, prior to their own repolarization. The cardiac APD is long (178 ms) and there was a long length of time for cardiac cells to charge their downstream neighbor, before the charging cell repolarizes. Decreasing intercellular coupling increased the time necessary to charge adjoining cells. The ratio of intercellular coupling reduction to still allow cell-to-cell excitation in homogeneous strands was 45:5:1 for the ventricular, skeletal myoblast, and skeletal myofiber cell types, respectively. In mixed strands, the limiting factor in excitation was any instance that the skeletal cell was the source cell.

These results demonstrate that: 1) the short skeletal action potential limits skeletal to cardiac conduction by limiting the capacity to provide a sufficient excitation charge to cardiac cells; 2) skeletal myoblast differentiation into myofibers further limits excitation capacity; 3) very high levels of gap-junction coupling are needed for successful skeletal to cardiac conduction.

Thus, conditions which decrease intercellular coupling will markedly decrease electrical transmission between transplanted skeletal cells and the adjoining myocardium. Electrical conduction slowing or block can lead to potential life threatening arrhythmias.

Example 2

Electrophysiologic Consequences of Skeletal Muscle Transplantation

To assess the electrophysiologic consequences of skeletal muscle transplantation into the myocardium, we utilized an in vivo model to assess cardiac conduction. The feasibility of gene transfer to specific areas of the cardiac conduction system has been previously demonstrated (Lee et al. 1198 PACE 21-II:606; Gallinghouse et al. November 1996 Am Heart Assoc.; U.S. Pat. No. 6,059,726). For example, the highly efficient and specifically localized expression of recombinant beta galactosidase in the AV node of rats and pigs has been described. The accuracy and reproducibility of AV nodal injections has been validated by the production of AV block in rats (Lee et al. 1998 J Appl Physiol. 85(2): 758-763). As an electrically insulated conduit for electrical transmission between the atrium and the ventricle, the AV conduction axis is in a strategic position for the study of cardiac electrophysiology.

To determine whether skeletal muscle transplantation alters conduction on AV nodal electrophysiologic properties, a rat model for AV node injections was utilized (Lee et al. 1998 J Appl Physiol. 85(2): 758-763). Animals were chemically denervated (using atropine and propranolol to inhibit the influence of autonomic nervous system) and studied with right atrial overdrive pacing and atrial programmed extrastimulation, both pre-injection and at the time of sacrifice. Surface ECG PR intervals were measured, together with AV nodal block cycle length (AVBCL) (the rate at which AV conduction becomes sequentially longer, then fails to conduct) and effective refractory period (ERP) (the coupling interval at which an atrial extrastimulus fails to conduct through the AV node). A single injection of skeletal myoblasts ($1\times10^5$, 15 ul) or vehicle was injected into the AVN of rats (n=8).

Electrophysiologic properties of the AV junction were significantly altered in animals with transplantation of skeletal myoblasts. Significant alterations in the Wenkebach cycle length (70.0±4.4 vs 57.0±5.0 msec; p<0.01) and AV nodal refractory period (113.8±5.6 vs 87.0±6.2 msec; p<0.005) were recorded in the skeletal myoblast injected rats as compared to control animals. Histological examination of the AVN revealed that approximately 10% of the AVN was involved with minimal to no inflammation. Histologically the AV conduction axis appeared normal in control vehicle injections. Interestingly, the PR interval did not significantly change, reflecting the insensitivity of surface EKG markers for cardiac conduction properties.

These results add further evidence that transplanted skeletal myoblasts (even when involving a small portion of the AVN) alters cardiac conduction and may lead to areas of slow conduction or conduction block. Therefore, as the skeletal myoblasts differentiate into myotubes and lose their ability to form gap junctions, the ability to propagate electrical impulses decrease.

Methods and Materials

The following materials and methods were utilized for Examples 3-7.

Skeletal Myoblast Isolation and Culture.

This protocol was approved by the Committee on Animal Research, University of California at San Francisco and conducted in accordance with federal guidelines. Neonatal skeletal myoblasts were isolated as previously described by enzymatic dispersion from 2-5 days old C3H neonatal mice and cultured as previously described (Rando, T., and Blau, H. M. (1994), J. Cell Biol. 125, 1275-1287). After isolation, cells were cultured with growth medium (GM) (80% F-10 medium (GIBCO BRL), 20% FBS (HyClone Laboratories, Inc.), penicillin G 100 U/ml and streptomycin 100 ug/ml,bFGF 2.5 ng/ml(human, Promega Corp)). Skeletal myoblasts were maintained in GM medium in humidified 95% air and 5% $CO_2$. Once the cultures achieved 75% confluency (day 0), the myoblasts were cultured in either GM medium or changed to differential medium (DM) (98% DMEM, 2% horse serum (HyClone), penicillin G 100 U/ml and streptomycin 100 ug/ml). Myoblasts cultured in DM were incubated in humidified 95% air and 10% $CO_2$. Myoblasts were collected on day 0, day 2, day 4, day 7, respectively for extraction of RNA and protein.

Production of Connexin 43

The rat connexin 43 (Cx43) cDNA was cloned into the MFG retroviral vector; and transduced into murine myoblasts as previously described (Springer M L, Chen A S, Kraft P E, Bednarski M, Blau H M., Molecular Cell. 1998, 2:549-558). This vector has been shown to be stably expressed in muscle (Dhawan J, Pan L C, Pavlath G K, Travis M A, Lanctot A M, Blau H M, Science 1991:254, 1509-1512). Primary myoblasts already expressing the E. coli β-galactosidase (β-gal) gene (TR/Z) was used as control myoblasts (Springer, M. L., and Blau, H. M., Som. Cell Mol. Genet. 1997:23, 203-209).

Determination of mRNA Levels Using RT-PCR

RNA from the cultured cells was prepared using the Qiagen Kit, Qiagen, Inc. CA, and quantified by spectrophotometry (A260 and A280 measurements). RNA (1 ug) of each sample was reverse-transcribed for 1 hour at 37° C. using Olig-dT and the same amount of cDNA was amplified for connexin 43, myogenin, myoD, desmin and GAPDH, respectively. The different primers used in this study were described in Table 2. After denaturing at 94° C. for 5 minutes, amplification was performed for certain cycles (94° C. for 30", 55° C. for 30" and 72° C. for 30"), followed by 72 cycles for another 5 minutes. The optimal cycles to semi-quantify the product for GAPDH and connexin 43 were 25; and for myogenin, myoD and desmin were 22. The PCR products were resolved by electrophoresis on 2% agrose gel and analyzed by densitometry with NIH software. The levels of connexin 43, myogenin, myoD, and desmin expression were normalized to the level of GAPDH; and the level of day 0 was set as 1.

chain protein was detected with Mf-20 antibody (Developmental studies hybridoma bank, University of Iowa) (1:2000 dilution). P21 protein was detected with P21 antibody (Chemicon international, Inc. Cz.) (1:500 dilution).

Immunofluoresence Analysis

Immunofluorescence method for connexin 43, MHC, Desmin were performed as described by Tomakidi P, Cheng H, Kohl A, Komposch G, Alonso A, Cell Tissue Res, 2000; 301(2):323-327. Briefly, myoblasts were plated on chamber slides with GM medium. At 70-80% confluence, the medium was either maintained in GM or switched to DM. Cells were collected on day 0, day 2, day 4 and day 7. After fixation with 4% paraformaldehyde in PBS and post fixative permeabilization with 0.2% triton X-100/PBS, cells were blocked with 3% BSA for 1 hour and incubated with primary antibody at room temperature for 1 hour. After washing with PBS three times, FITC-conjugated secondary antibody were used for incubation 1 hour. The dilution for Desmin antibody (Sigma, St. Louis, Mo.), connexin 43 (Zymed Laboratories, Inc. Ca.) and MF-20 (Developmental studies hybridoma bank, University of Iowa) were 1:100, 1:100 and 1:50, respectively.

Microinjection Technique

Gap junctions were evaluated by microinjecting cells with the gap junction permeable dye, Lucifer yellow (Molecular Probes, Oreg.). Microinjection was performed in: 1) control (TR/Z) and CX43 myoblasts at 70-80% confluency, 2) TR/Z and CX43 myotubes and 3) co-cultured adult rat cardiomyocytes (ARC) and adult skeletal myoblasts or myotubes. The dye solution was composed of 2% Lucifer yellow (gap junction permeable) and 1% tetramethylrhodamine-dextran (gap junction impermeable; Molecular Probes) in sterile distilled water. Microinjection was performed with Micromanipulator 5171, FemtoJet, Eppendorf by a pulse pressure of 80 hpa of 0.3 second of duration through a 0.5±0.2 μm tip micropipette (Femtotips, Eppendorf). Cultured cells were washed and the medium was replaced with phosphate-buffered saline (PBS)

TABLE 2

Summary of Primers utilized in Experimental studies:

| Genes | Primer (Forward) | Primer (Reverse) |
|---|---|---|
| Connexin 43 | 5'-TACCACGCCACCACCGGCCCA-3' (SEQ ID NO. 1) | 5'-GGCATTTTGGCTGTCGTCAGGGAA-3' (SEQ ID NO. 2) |
| Myogenin | 5'-CCTTAAAGCAGAGAGCATCC-3' (SEQ ID NO. 3) | 5'-GGAATTCGAGGCATAATATGA-3' (SEQ ID NO. 4) |
| MyoD | 5'-TTCTTCACCACACCTCTGACA-3' (SEQ ID NO. 5) | 5'-GCCGTGAGAGTCGTCTTAACTT-3' (SEQ ID NO. 6) |
| Desmin | 5'-CCGGAGGCTTGGGGTCGCT-3' (SEQ ID NO. 7) | 5'-CTGTTCCTGAAGCTGGGCCTGG-3' (SEQ ID NO. 8) |
| GAPDH | 5'-AAAGTGGAGATTGTTGCCAT-3' (SEQ ID NO. 9) | 5'-TTGACTGTGCCGTTGAATT-3' (SEQ ID NO. 10) |

Detection of Protein Expression with Western Blotting

The total soluble protein was extracted from the cultured cells and was quantified by Bradford method. The soluble proteins (40 μg) were separated via SDS-PAGE using a 10-20% resolving gel for connexin 43, MHC, P21 detection. Proteins were electroblotted to HYBOND™-ECL nitrocellulose membrane and immunoreactions were carried out as described using the ECL detection kit. Connexin 43 was detected using as anti-connexin 43 rabbit polyclonal antibody (Zymed Laboratories, Inc. Ca.) (1:1000). Myosin heavy containing 10% FBS. Injections were done with Nikon TE300 Microscope with phase and fluorescence optics.

Example 3

Expression of Gap Junction Proteins

Connexin 43-encoding nucleic acid was introduced into skeletal muscle cells as described above. The formation of functional gap junctions between recombinant Cx43-expressing myoblasts or recombinant Cx43-expressing myoblasts which have differentiated into myotubes with other types of myoblasts or myotubes was evaluated. A control (TR/Z) myoblast cell, which expresses Cx43 initially and then down regulates Cx43 expression during differentiation into myotubes was utilized as a control for functional gap junctions and dye transfer in control myoblast but not in control myotubes.

Figure 2A:
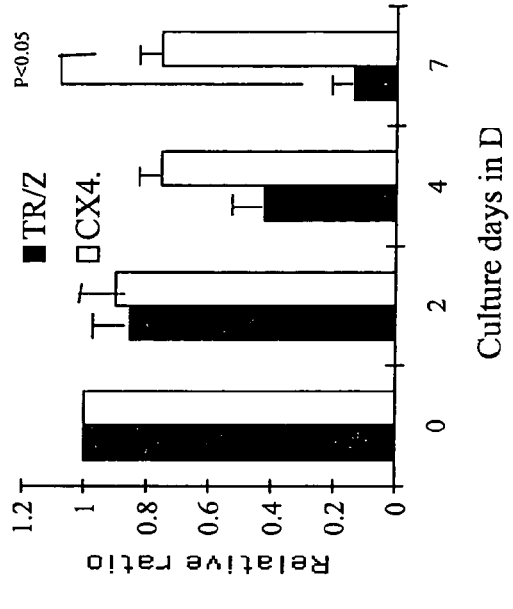
FIG. 2A is a photograph of an electrophoresis agarose gel of mRNA Cx43 RT-PCR experiments of control cells (TR/Z) and recombinant Cx43-expressing cells at day 0, 2, 4 and 7.
Figure 2B:
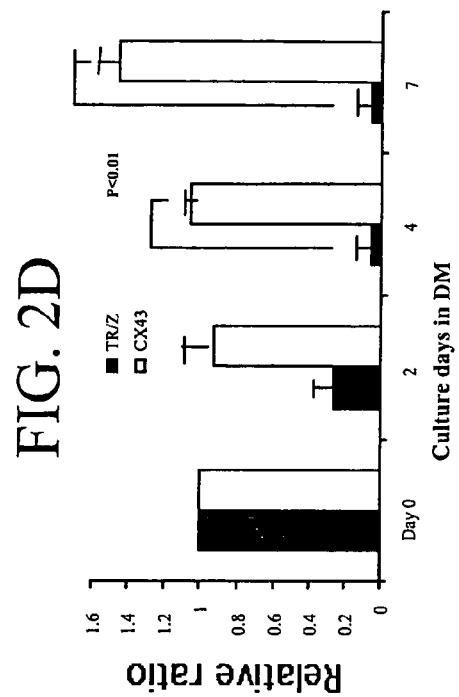
FIG. 2B is a graphical representation of the average level of Cx43 mRNA determined by RT-PCR for three control samples and three recombinant Cx43-expressing cell samples at day 0, 2, 4 and 7.

In FIGS. 2A-2D, the Cx43 mRNA (FIGS. 2A and B) and protein changes (FIGS. 2C and D) in control cells and Cx43 cells are shown. FIG. 2A is a photograph of an electrophoresis agarose gel of RT-PCR experiments indicating the mRNA Cx43 levels of control cells (TR/Z) and recombinant Cx43-expressing cells at day 0, 2, 4 and 7. FIG. 2B is a graphical representation of the average level of Cx43 mRNA determined by RT-PCR for three control samples and three recombinant Cx43-expressing cell samples at day 0, 2, 4 and 7. FIG. 2A and 2B show that the connexin 43 mRNA levels were significantly down-regulated by day 7 in TR/Z control (untransformed) skeletal myotubes while in contrast, the Cx43-modified cells exhibited no significant difference in Cx43 mRNA expression between day 0 and day 7, indicating that retroviral transduction with the connexin 43 gene was accomplished and Cx43 was expressed in mature myotubes unlike control myotubes (Day 7).

Figure 2C:
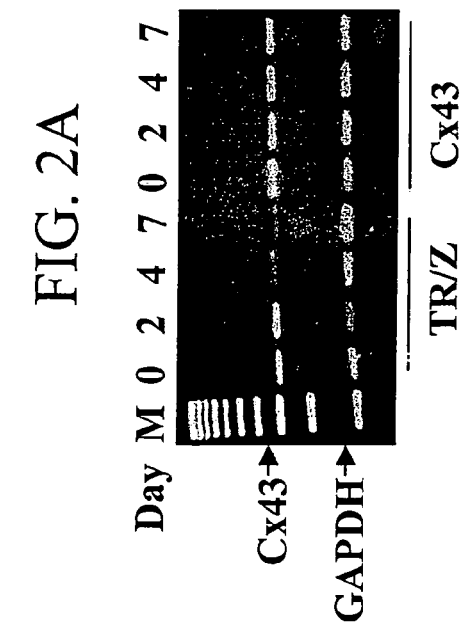
FIG. 2C is a photograph of a western blot for Cx43 protein, which indicates the relative amounts of Cx43 protein present in control cells and recombinant Cx43-expressing cells at day 0, 2, 4 and 7.
Figure 2D:
FIG. 2D is a graphical representation of Cx43 western blotting experiments to determine the relative amount of Cx43 protein in three control cell samples and three Cx43 expressing cell samples at day 0, 2, 4 and 7.

FIGS. 2C and 2D show the Cx43 protein levels associated with the same cells analyzed for Cx43 mRNA depicted in FIG. 2A and 2B. FIG. 2C is a photograph of a western blot for Cx43 protein, which indicates the relative amounts of Cx43 protein present in control cells and recombinant Cx43-expressing cells at day 0, 2, 4 and 7. FIG. 2D is a graphical representation of Cx43 western blotting experiments to determine the relative amount of Cx43 protein in three control cell samples and three Cx43 expressing cell samples at day 0, 2, 4 and 7. Protein expression results were consistent with the RT-PCR results confirming that expression of recombinant Cx43 can rescue connexin 43 loss in control cells at day 7 (FIG. 2C and 2D). The RT-PCR results shown in FIG. 2A and 2B, demonstrate that Cx43 mRNA levels as expected, in control cells were gradually down and almost absent at day 7 while the level of Cx43 mRNA for recombinant CX43 expressing cells was unchanged through day 0 to day 7. GAPDH was utilized as an internal control in these RT-PCR studies. Western blotting with antibodies for Cx43, in control cells showed that CX43 expression was downregulated at day 2 and almost absent after day 4 (during myotube formation) while recombinant Cx43-expressing cells did not show any downregulation, and even upregulation could be detected at day 7. No differences in N-cadherin mRNA and protein expression levels were found in skeletal myoblasts before or after differentiation.

Figure 3:
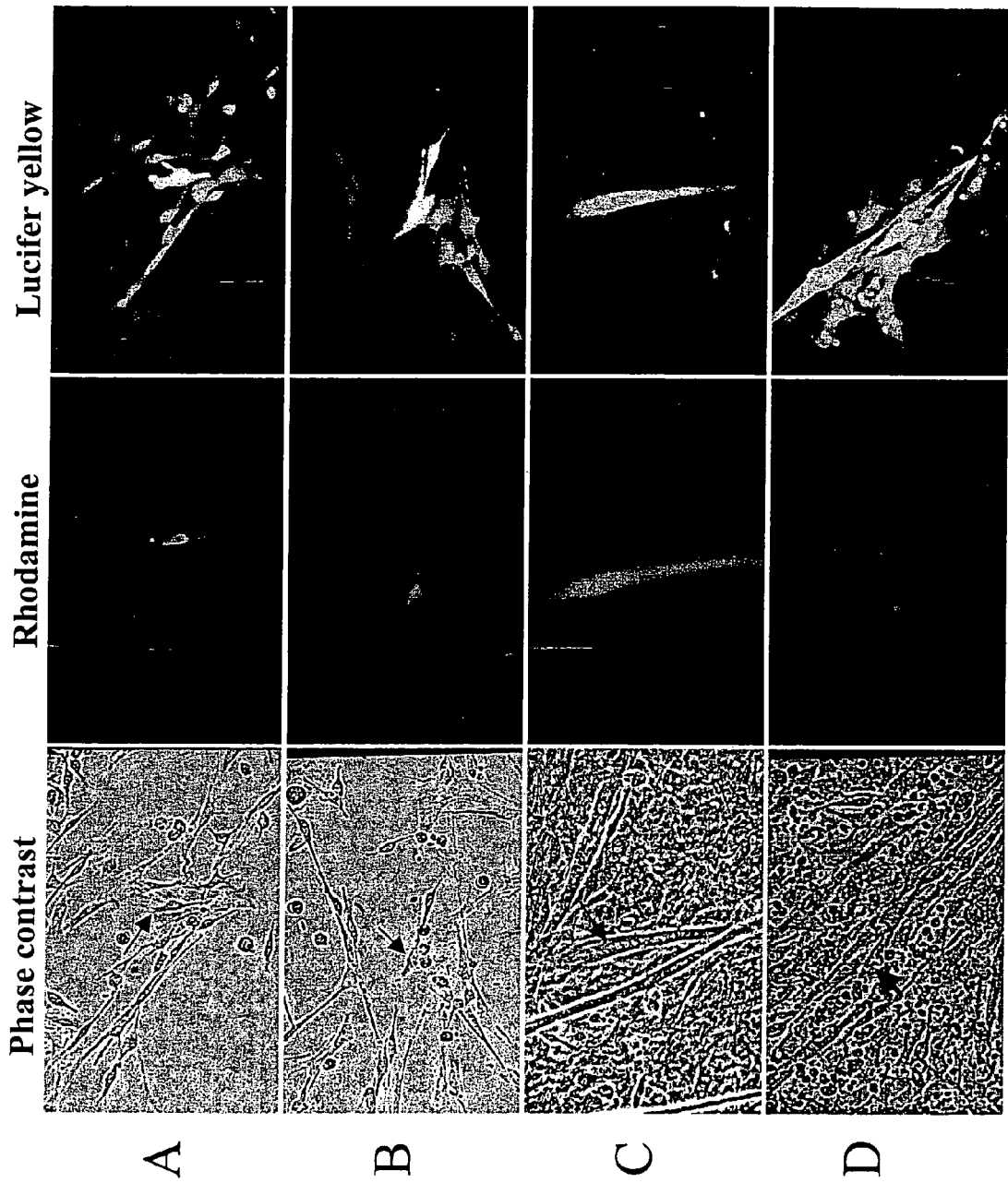
FIG. 3 is a series of photographs showing the results of a microinjection study between skeletal myoblasts or myotubes indicating the relative transfer of Rhodamine or Lucifer yellow dyes. Row A: control myoblasts to control myoblasts; row B: Cx43 myoblasts to Cx43 myoblasts; row C: control myotube to control myotube; row D: Cx43 abnormal myotube to Cx43 abnormal myotubes.

Microinjection studies to investigate the formation of functional gap junctions were completed on control cells (myoblast and myotubes) and recombinant Cx43-expressing cells (myoblasts and myotubes). Injected cells were labeled with rhodamine dextron and Lucifer Yellow, Lucifer yellow being capable of transfer from one cell to another through functional gap junctions. The black arrow in the phase contrast panels of FIG. 3 indicates the injected cell in each set of experiments. FIG. 3 shows photographs of a microinjection study between skeletal myoblasts or myotubes indicating the relative transfer of Rhodamine or Lucifer yellow dyes. Each panel of FIG. 3 shows the cells of interest under phase contrast microsopy and appropriate fluorescence illumination for either Rhodamine or Lucifer yellow fluorescent dyes, FIG. 3 row A is a photograph of control myoblasts which express Cx43, contacting other control myoblasts; row B is a photograph of Cx43 myoblasts to Cx43 myoblasts; row C shows control myotube (no Cx43 expression) to control myotube and row D shows photographs of Cx43 myotube to Cx43 myotubes.

These microinjection studies show that in skeletal myoblasts, dye transfer (Lucifer yellow) could be observed in both control (TR/Z) and Cx43 myoblasts (FIG. 3, :rows A and B). After 7 days in culture with DM media, no dye transfer could be observed in myotubes formed from control myoblasts, FIG. 3, :row C. Dye transfer persisted in Cx43 transduced skeletal cells placed in differentiation media for 7 days (FIG. 3, :row D). In summary, these microinjection experiments showed that dye transfer occured in Cx43 transduced skeletal myoblasts placed in differentiation media and not in control myotubes.

Example 4

Gap Junction Function and Co-culture Experiments

To evaluate gap junction formation between myoblasts and cultured adult rat cardiomyocytes (ARC), single adult rat cardiac ventricular myocytes were enzymatically isolated from female Sprague-Dawley rats weighing 200-250 g by standard methods. Briefly, following intraperitoneal anesthesia (pentobarbtal 100 mg/kg), the rat heart was rapidly excised and perfused retrogradely via the aorta using the Langendorff technique. The perfusion was performed at 37° C. using solution A (norminal $Ca^{2+}$ free solution, NaCl 134 mM, KCl 5.4 mM, Hepes 10 mM, glucose 10 mM, $MgCl_2$ 1 mM, NaH2PO4 0.33 mM, titrated to pH 7.4 with NaOH.) for 5 min, solution A, 0.1 mM $CaCl_2$ with 1 mg/ml collagenase (Type B, Boehringer Mannheim, Germany) for about 15 min consequently, then washout with solution A and CaCl2 0.2 mM for 5 min. Afterwards the left ventricle was removed and chopped into small pieces, which were incubated with 20 ml solution A and 0.1 mM $CaCl_2$ with shaking at 37° C. for 10 min in a glass conical flask. The cell suspension was filtered (200 micron mesh) and the filtrate was sedimented for 5 min. The $Ca^{2+}$ concentration of the supernatant was gradually increased with 1 mM $Ca^{2+}$-containing solution till 0.5 mM final concentration. ARC were grown in HAM-F-12/M199 (1:1) supplemented with 10% FBS, penicillin G 100 U/ml and streptomycin 100 µg/ml in laminin-coated dishes at densities of $10^4$ rod-shaped cells $cm^{-2}$.

In serum-containing medium, ARC undergo a morphological change described as dedifferentiation/redifferentiation, hallmarked by the loss of the rod shape and myofibrillar disintegration and subsequent spreading, and reorganization of the contractile apparatus. On day 3, cytosine arabinouranoside (5 µM) was added to prevent fibroblasts overgrowth. Most of the ARC were redifferentiated by day 7 and contractile activity was observed. After completion of differentiation/redifferentiation, skeletal myoblasts ($10^4$/cm2) were added to the ARC cultures. They were kept in the HAM-F-12/M199 medium for overnight and microinjection was performed next day to evaluate dye transfer between myoblast and ARC. To induce myotubes formation, the medium was changed to DM and microinjection was performed after myotubes formation (7 days).

Microinjection studies to investigate the formation of functional gap junctions between cardiomyocte cells and control cells (skeletal myoblast and myotubes) or with recombinant Cx43-expressing cells (skeletal myoblasts and myotubes) were completed. Injected cells were labeled with rhodamine dextron and Lucifer Yellow, Lucifer yellow being capable of transfer from one cell to another through functional gap junctions. The black arrow in FIG. 4 indicates the injected cell in each set of experiments. In co-culture experiments, dye transfer could be observed between adult rat cardiomyocytes (ARC) and control myoblast (which express Cx43, FIG. 4, row A) or with Cx43 myoblasts (FIG. 4, row B). Even after 7 days in differentiation culture, Cx43 cells were capable of dye transfer with ARC, indicating functional gap junctions (FIG. 4, row D). In contrast, there was no dye transfer between control skeletal myotubes and ARC as shown in FIG. 4, row C. In summary, these experiments indicate the unique and novel features of the present invention by demonstrating that it is possible to form functional gap junctions between two different cell types by expressing a recombinant connexin in one of the cells. In particular, that functional gap junctions can be formed between adult skeletal muscle cells modified to over express Cx43 and cardiomyocytes.

Example 5

Effects of Connexin 43 Expression on Skeletal Myoblasts Differentiation

To determine the effect of Cx 43 expression on the differentiation of skeletal myoblasts, expression levels of other proteins were analyzed. FIG. 5 shows the results from an Immunofluorescence study analyzing the expression levels of MHC and Desmin, two strong markers for myoblast differentiation into myotubes, in control and Cx43 cells (MHC: FIG. 5, upper panel and Desmin: FIG. 5, lower panel). Control skeletal myoblasts differentiated into multinucleated myotubes after incubation with DM for 7 days. In the Connexin 43 group, myotubes did not form even after 14 days in DM. Clearly, expression of recombinant Cx43 prevented myoblasts from forming myotubes. Immunofluorescence studies shown in FIG. 5 demonstrate that MF-20 (MHC) and Desmin, two strong markers for myoblast differentiation into myotubes, were present at day 7 in control samples and absent in the CX 43 expressing samples. The MHC and Desmin results are shown in the upper and lower panels of FIG. 5, respectively. MF-20 expression from western blotting study was consistent with immunofluorescent study. P21 expression, marker of cell mitosis arrest, had consistent changes among these groups and was up-regulated gradually from day 0 to day 7, which reflects that both TR/Z and Cx43 cells withdraw from dividing when medium was switched to DM.

To determine whether the expression of recombinant connexin 43 is harmful to myotubes or is only deleterious during differentiation from myoblasts to myotubes, skeletal myoblasts and myotubes were transfected with a replication-deficient adenovirus with the Cx43 gene (Ad Cx43). Myoblasts transfected with Ad Cx43 and transferred to differentiation media had impaired myotube formation. In contrast, fully differentiated myotubes transfected with Ad Cx43 remained normal appearing and aligned themselves in an orderly array analogous to control myotubes. Transfection with control adenovirus without Cx43 developed normally.

Example 6

Cx 43 Expression in Skeletal Muscle Improves Electrical Conduction in the AV Node To determine whether the forced expression of connexins improve cardiac conduction, skeletal muscle cells were transduced with Cx 43 (same cells as used in in vitro experiments) and injected into the AV node of immunodeficient rats (Lee et al. 1998 J Appl Physiol. 85(2): 758-763). Animals injected with Cx 43 transduced skeletal myoblasts ($2.5 \times 10^6$ cells/ 25 µl; n=8) were compared to animals injected with control skeletal myoblasts ($2.5 \times 10^6$ cells/ 25 µl; n=5). Surface ECG PR intervals were measured, together with AV nodal block cycle length (AVBCL) (the rate at which AV conduction becomes sequentially longer, then fails to conduct) and AVN effective refractory period (AVN ERP) (the coupling interval at which an atrial extrastimulus fails to conduct through the AV node).

Significant shortening of the PR interval was observed in the animals injected with Cx43 transduced skeletal myoblasts as compared to the control skeletal muscle cell injected animals (40.6±1.9 ms vs 47.6±2.5 ms; p<0.0001, paired T-test). The AVBCL (96.7±10 ms vs 112.0±11.0 ms; p<0.03, paired T-test) and AVN ERP (80.0±9.2 ms vs 100.0±16.0 ms; p<0.001, paired T-test) were significantly improved in animals injected with Cx43 transduced skeletal myoblasts as compared to animals injected with control skeletal myoblast These results demonstrate that the electrical conduction through the AV junction was significantly improved in animals injected with Cx43 transduced skeletal myoblasts as compared to control skeletal myoblasts. Thus connexin production in the recombinant cells provided for electrical connection between the recombinant cells and adjoining myocardial cells, which in turn would provide for better electromechanical synchrony between the atria and the ventricle.

Example 7

Autologous Transplantation of Cx43-Expressing Cells in Patients with a Previous Myocardial Infarction The treatment of cardiomyopathy in humans is carried out as follows. A muscle biopsy is obtained from patients who have experienced anterior, lateral or inferior wall myocardial infarction and may or may not be a patient that requires coronary artery bypass graft (CABG) surgery. The skeletal muscle cells gathered from the biopsy are cultured ex vivo and genetically modified to express a human connexin (such as Cx43) by the methods described above. The modified skeletal muscles are analyzed for recombinant connexin expression by immunofluorescence assay for connexin protein. In certain instances, the cells are analyzed for the ability to form functional gap junctions with cardiomyocyte cells by the in vitro Lucifer dye assays described above.

After analysis of the modified muscle cells, a therapeutically effective amount of the modified muscle cells are implanted into the patients heart tissue. In certain instances when the patients own skeletal muscle cells cannot be used for cardiac treatment, a recombinant muscle cell line which expresses recombinant human Cx43 is utilized in conjunction with the appropriate use of immunosuprression drugs known to those skilled in the art. The Cx43 expressing muscle cells are then implanted endovascularly with a injection catheter, which catheters can be obtained from a variety of sources (e.g., injectable catheters such as Johnson & Johnson's NOGA system, BioHeart's Myocath, Biocardia, Boston Scientific's stilleto, Transvascular catheter, and the like) or with a hypodermic syringe for a CABG procedure. The patient is monitored after surgery to evaluate the efficacy of treatment.

Patients

The patients are males and females generally between 18 and 75 years of age with the diagnosis of previous myocardial infarction or non-ischemic cardiomyopathy.

Biopsy

The skeletal muscle biopsy is obtained within a few weeks (e.g., 3-4 weeks) of anticipated coronary artery bypass for patient where the procedure is warranted. Autologous skeletal muscle cells (myoblasts and myotubes) are isolated from the skeletal muscle biopsy. Under sterile surgical conditions, an open biopsy technique is utilized to excise skeletal muscle from the muscle belly. The biopsy is obtained from the thigh (Quadriceps-vastus lateralis) or the mid-calf (Gastrocnemius) of the patient. An attempt is made to exclude contaminating fascia from the biopsy.

Quadriceps-vastus lateralis—An incision is made longitudinally along the anterolateral aspect of the thigh in the lower third of the thigh. Dissection is carried through the soft tissue and fascia and the quadriceps vastus lateralis will be identified and exposed. A segment of muscle is resected longitudinally along the long axis of the muscle fiber and placed into a container of transport medium.

Gastrocnemius—An incision is longitudinally in the posterolateral gastrocnemius area in the mid calf. Dissection is made through to the deep fascia to expose the gastrocnemius muscle. A segment of muscle is resected longitudinally along the long axis of the muscle fiber and placed into a container of transport medium.

Ex vivo Propagation and Genetic Modification of Autologous Cells

The methods and protocols used for the isolation, expansion and transduction of the autologous skeletal muscle cells with a human connexin construct ex vivo are as described above. For example, human connexin (e.g., Cx43) cDNA is cloned into the MFG retroviral construct and transduced into the autologous skeletal mucslce cells in a similar manner as described by Springer M L et. al., Molecular Cell. 1998, 2:549-558. This construct is generally stably expressed in the autologous muscle cells.

The genetically modified cells are cultured so as to provide for a concentration of about $10^6$-$10^9$ cells/ml. The modified cells may be stored under refrigeration (usually around 0° C.) prior to transplantation into the patient. Cell viability via Trypan Blue Dye Exclusion can be used as a cell viability assay. Potency is confirmed via the detection of Cx43 expression by immunofluorescence and/or by the functional gap junction assays described above.

Implantation of Recombinant Connexin Expressing Cells via a Percutaneous Approach Implanting the recombinant connexin expressing cells into the myocardium involves administering the recombinant cells by using a catheter delivery system. The recombinant cells are injected into the akinetic myocardial scar at the site of a previous infarct. Depending on the size of the targeted infarct zone, between 400 million and 1 billion cells are injected as a suspension. Multiple injections can be used to deliver the recombinant cells.

The injections are carried out by advancing the needle through the end hole of the catheter to a predetermined depth. The proximal end of the needle lumen is attached to a calibrated syringe that contains the recombinant cell suspension. After adequate positioning against the endocardial surface by fluoroscopic, intracardiac echocardiography or magnetic resonance imaging guidance, the needle is advanced into the myocardium and the cell suspension is injected. Upon completion of the injection, the needle is withdrawn into the catheter. This method is repeated in the target region until transfer of the cells is complete. An attempt is made to cover the entire area of the scar, including its periphery. If the cellular therapy is delivered during a CABG, then a needle and syringe are used to epicardially deliver the cells to the akinetic region as described above.

Monitoring and Evaluation of Treatment

Clinical status, adverse events, 12-lead electrocardiogram, 24 hour ambulatory electrocardiogram, and routine clinical laboratory tests are carried out by methods and techniques known to those skilled in the art for the evaluation of regional left ventricular wall function. Follow-up can be performed and compared to baseline (i.e., prior to treatment) at selected periods post-implantation (e.g., 1, 2, 3, 4, 6, and 12 months). In certain instances, evaluation of treatment may include Dobutamine stress echocardiographic evaluation of regional wall motion and wall thickness in region of implantation (infracted region), contrast ventriculography or magnetic resonance imaging. The monitoring and evaluation post treatment can be used to determine the level of regeneration of functional muscle and synchronized electromechanical conduction within the infarct.

Example 8

Autologous Transplantation of Recombinant Cx43-Expressing Cells in Patients with Cardiac Conduction Disease Patients The patients are males and females between 1 and 90 years of age with the diagnosis of cardiac conduction disease (i.e., heart block). The heart block can be congenital, acquired, iatrogenic (e.g., as a complication of valve surgery or catheter ablation) or part of the normal aging process. Utilizing the methods described in Example 7, 1-100 million modified cells can be injected in the AV node region in a volume of 0.2-0.5 ml. The recombinant connexin cells can be delivered surgically via a 25 gauge syringe, via the AV nodal artery or via a percutaneous delivery system (see, e.g., U.S. Pat. No. 6,059,726.

Monitoring and Evaluation of Treatment

The detection of heart block (and its treatment) can be readily detected by surface ECG. Exercise stress testing, holter monitoring or an electrophysiology study are alternative supplemental tests to assess therapy.

That which is claimed is:

1. A method of establishing an electrical connection between a recombinant mammalian cell and a myocardial cell, the method comprising:
    contacting a myocardial cell of a subject with a recombinant mammalian cell genetically modified to express a connexin 43 protein;
    wherein the recombinant mammalian cell is a skeletal muscle cell or a mesenchymal stem cell, and wherein the cell is autologous or allogenic to the subject, and wherein said contacting is performed by injection into cardiac tissue of the subject, or is performed by cardiovascular infusion into the subject, and is sufficient to establish an electrical connection between the myocardial cell and the recombinant mammalian cell.

2. The method of claim 1, wherein the recombinant mammalian cell is, a mesenchymal stem cell.

3. The method of claim 1, wherein the recombinant mammalian cell is a skeletal muscle cell.

4. The method of claim 3, wherein the skeletal muscle cell is an adult skeletal muscle cell.

5. The method of claim 1, wherein after the electrical connection between the recombinant mammalian cell and the myocardial cell is established, the recombinant mammalian cell has conductive characteristics similar to the myocardial cell.

6. A method of establishing an electrical connection between a recombinant skeletal muscle cell and a myocardial cell, the method comprising:
    contacting a myocardial cell of a subject with a recombinant skeletal muscle cell genetically modified to express a connexin 43 protein, wherein the recombinant cell is autologous or allogenic to the subject, and said contacting is performed by injection into cardiac tissue of the subject, or is performed by cardiovascular infusion, and is sufficient to establish an electrical connection between the myocardial cell and the recombinant skeletal muscle cell so that the recombinant skeletal muscle cell has conductive characteristics similar to the myocardial cell.

7. The method of claim 6, wherein the skeletal muscle cell is an adult skeletal muscle cell.

8. A method for treating a cardiac conduction disturbance in a host, the method comprising:
    introducing into cardiac tissue of said host a therapeutically effective amount of a recombinant mammalian cell genetically modified to express a connexin 43 proteins;
    wherein the recombinant mammalian cell is a skeletal muscle cell or a mesenchymal stem cell, and wherein the cell is autologous or allogenic to the host,
    wherein said introducing is performed by injection into cardiac tissue of the host, or is performed by cardiovascular infusion into the host, and
    wherein said introducing is effective to establish an electrical connection between the recombinant cell and a myocardial cell of the host cardiac tissue; and
    wherein the cardiac conduction disturbance in the host is treated.

9. The method of claim 8, wherein the recombinant cell is a skeletal muscle cell.

10. The method of claim 9, wherein the skeletal muscle cell is an adult skeletal muscle cell.

11. The method of claim 8, wherein said introducing comprises implanting the recombinant cell into an infarct region of the cardiac tissue.

* * * * *

SEQUENCE LISTING

<160> NUMBER OF SEQ ID NOS: 10

<210> SEQ ID NO 1
<211> LENGTH: 21
<212> TYPE: DNA

<213> ORGANISM: Artificial Sequence
<220> FEATURE:
<223> OTHER INFORMATION: primer

<400> SEQUENCE: 1
taccacgcca ccaccggccc a                                    21

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ggcattttgg ctgtcgtcag ggaa                                 24

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ccttaaagca gagagcatcc                                      20

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ggaattcgag gcataatatg a                                    21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
ttcttcacca cacctctgac a                                    21

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6
gccgtgagag tcgtcttaac tt                                   22

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
ccggaggctt ggggtcgct                                       19

-continued

```
<210> SEQ ID NO 8
<211> LENGTH: 22
<212> TYPE: DNA
<213> ORGANISM: Artificial Sequence
<220> FEATURE:
<223> OTHER INFORMATION: primer

<400> SEQUENCE: 8
ctgttcctga agctgggcct gg                                              22

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
aaagtggaga ttgttgccat                                                 20

<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
ttgactgtgc cgttgaatt                                                  19
```